(12) United States Patent
Kim et al.

(10) Patent No.: US 11,147,519 B2
(45) Date of Patent: Oct. 19, 2021

(54) MAGNETIC RESONANCE IMAGING APPARATUS FOR GENERATING PARAMETRIC MAP FROM MAGNETIC RESONANCE SIGNAL DATA AND METHOD OF OPERATING THE SAME

(71) Applicants: SAMSUNG ELECTRONICS CO., LTD., Suwon-si (KR); SEOUL NATIONAL UNIVERSITY R&DB FOUNDATION, Seoul (KR)

(72) Inventors: Youngbeom Kim, Suwon-si (KR); Doohee Lee, Seoul (KR); Jongho Lee, Seoul (KR); Junki Lee, Suwon-si (KR); Sangyoung Zho, Suwon-si (KR)

(73) Assignees: SAMSUNG ELECTRONICS CO., LTD., Suwon-si (KR); SEOUL NATIONAL UNIVERSITY R&DB FOUNDATION, Seoul (KR)

( * ) Notice: Subject to any disclaimer, the term of this patent is extended or adjusted under 35 U.S.C. 154(b) by 123 days.

(21) Appl. No.: 16/426,225

(22) Filed: May 30, 2019

(65) Prior Publication Data
US 2020/0345311 A1    Nov. 5, 2020

(30) Foreign Application Priority Data

Apr. 30, 2019    (KR) .................. 10-2019-0050983

(51) Int. Cl.
*G01R 31/01*    (2020.01)
*A61B 5/00*    (2006.01)
*A61B 5/055*    (2006.01)
*G01R 33/56*    (2006.01)
*G01R 33/50*    (2006.01)
*G06F 30/20*    (2020.01)

(52) U.S. Cl.
CPC ............ *A61B 5/7267* (2013.01); *A61B 5/055* (2013.01); *G01R 33/50* (2013.01); *G01R 33/5608* (2013.01); *G06F 30/20* (2020.01)

(58) Field of Classification Search
USPC .............................. 324/307, 309, 316, 76.51
See application file for complete search history.

(56) References Cited

U.S. PATENT DOCUMENTS

2015/0006114 A1    1/2015    Altbach et al.
2020/0311878 A1*   10/2020   Matsuura ............. G06K 9/4628

OTHER PUBLICATIONS

Doohee Lee et al., "SafeNet: Artificial Neural Network for Real-Time T2 Mapping with Quality Assurance", ISMRM, Jun. 1, 2018, retrieved from URL: https://submissions.mirasmart.com/ISMRM2018/ViewSubmissionPublic.aspx?sei=N1H7WtRBu, retrieved on Nov. 10, 2017, 4 pages.

(Continued)

*Primary Examiner* — Vincent Q Nguyen
(74) *Attorney, Agent, or Firm* — Sughrue Mion, PLLC

(57) ABSTRACT

Imperfect RF pulses in a multi-spin-echo (MSE) sequence disturb prediction of relaxation times. Provided are a magnetic resonance imaging (MRI) apparatus and method of operating the same, whereby a characteristic parameter value may be acquired from MR signal data via training using an artificial neural network (ANN) and a parametric map may be generated based on the acquired characteristic parameter value. The ANN may be trained to compensate for imperfect RF pulses while providing reduced computation times to produce an output image.

18 Claims, 12 Drawing Sheets

(56) References Cited

OTHER PUBLICATIONS

Cohen, Ouri et al., MR fingerprinting Deep RecOnstruction NEtwork (DRONE), Magnetic Resonance in Medicine, Mar. 5, 2018, vol. 80, pp. 885-894. (10 pages total).
Lee, Doohee et al., "Single-Scan Z-Shim Method for Reducing Susceptibility Artifacts in Gradient Echo Myelin Water Imaging", Magn Reson Med., 2018, vol. 80, pp. 1101-1109, https://doi.org/10.1002/mrm.27127.
Cai, Congbo et al., "Single-shot T2 mapping using overlapping-echo detachment planar imaging and a deep convolutional neural network", Magnetic Resonance in Medicine, 2018, vol. 80, pp. 2202-2214. (13 pages total).

\* cited by examiner

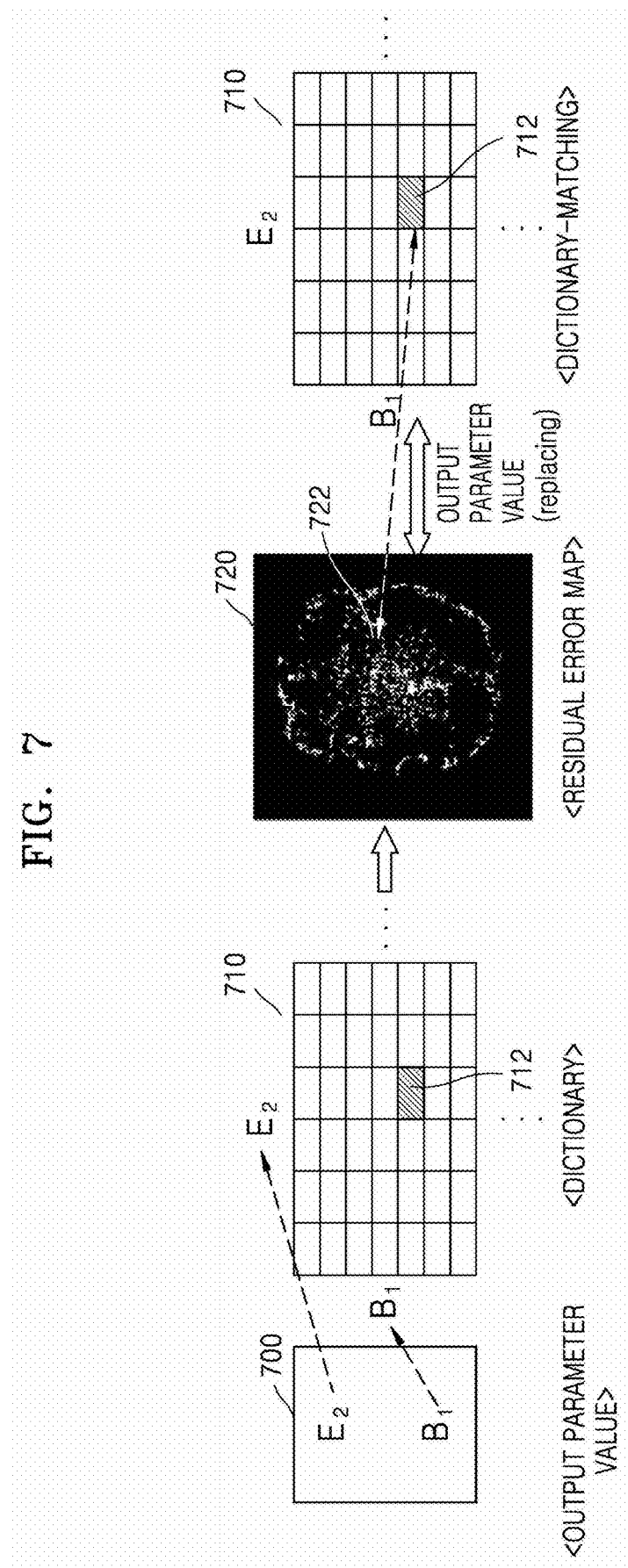

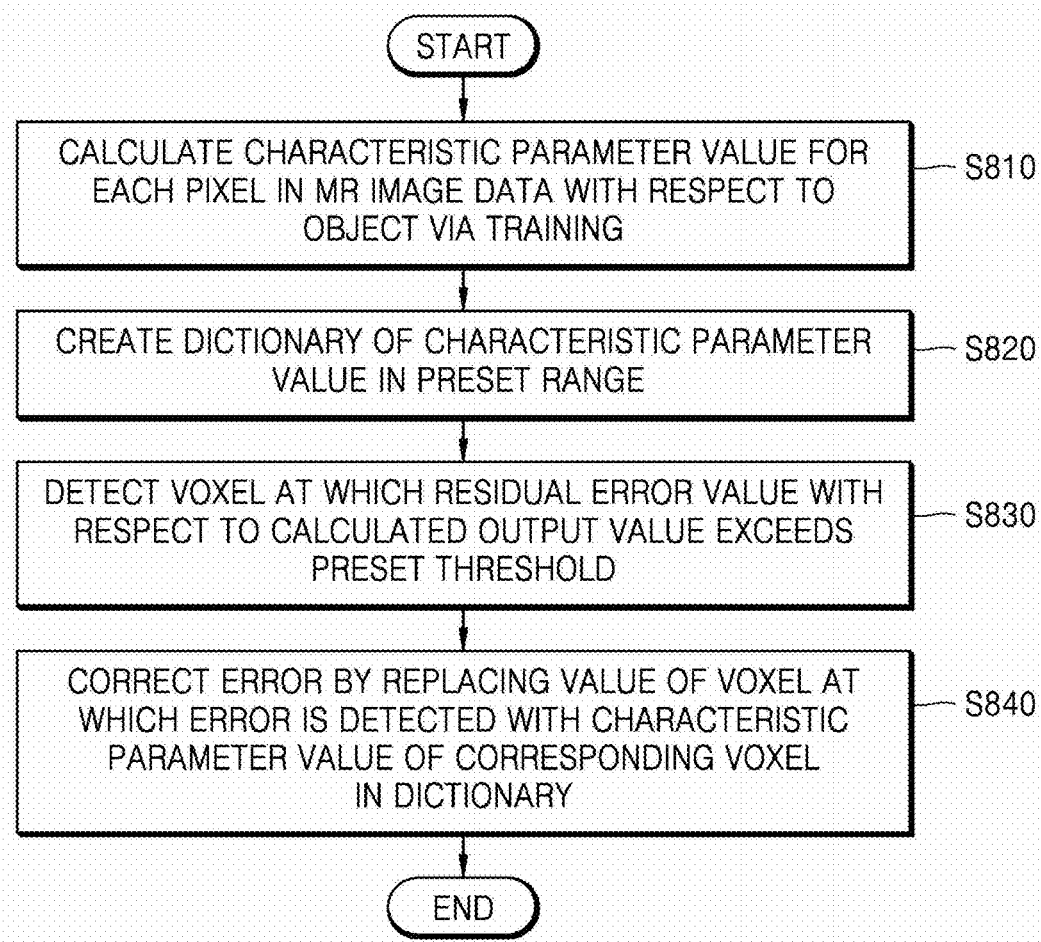

MAGNETIC RESONANCE IMAGING APPARATUS FOR GENERATING PARAMETRIC MAP FROM MAGNETIC RESONANCE SIGNAL DATA AND METHOD OF OPERATING THE SAME

CROSS-REFERENCE TO RELATED APPLICATION(S)

This application is based on and claims priority under 35 U.S.C. § 119 to Korean Patent Application No. 10-2019-0050983, filed on Apr. 30, 2019, in the Korean Intellectual Property Office, the disclosure of which is incorporated by reference herein in its entirety.

BACKGROUND

1. Field

The disclosure relates to magnetic resonance imaging (MRI) apparatuses for generating a parametric map from magnetic resonance signal data.

2. Description of Related Art

A magnetic resonance imaging (MRI) apparatus use a magnetic field to capture an image of an object. MRI apparatuses have been widely used for accurate disease diagnosis because stereoscopic images of bones, lumbar discs, joints, nerves, ligaments, the heart, etc. can be obtained at desired angles. MRI may provide MR images having various contrasts by adjusting multiple characteristic parameters. In clinical diagnosis, MRI is used to obtain images of the same region of an object with different contrasts and diagnose conditions of the object.

Examples of a parametric map generally used for MR imaging-based diagnosis include a T1 map, a T2 map, a T1rho map, a proton density (PD) map, etc. A parametric map is an image obtained by reflecting the extent of decay of an MR signal from tissue of an object being imaged due to spin relaxation, and may be used for diagnosis of the brain, cardiac muscles, lesions, cartilage degradation, etc. by quantifying a T1 or T2 value (msec) of the tissue.

T1 and T2 are time constants useful for tissue characterization in MRI. T1 (longitudinal relaxation time) is a time constant which may determine the rate at which excited protons return to equilibrium. T1 may be a measure of the time taken for spinning protons to realign with the external magnetic field. T2 (transverse relaxation time) may be the time constant which determines the rate at which excited protons reach equilibrium or go out of phase with each other. T2 may be a measure of the time taken for spinning protons to lose phase coherence among nuclei spinning perpendicular to the main field.

To generate a parametric map, quantification of characteristic parameters of tissue is needed. An MR signal modeling equation is used for the quantification of characteristic parameters. The MR signal modeling equation may vary depending on mapping parameters to be calculated. In general, an MR signal modeling equation is an equation for calculating a mapping parameter by modeling a magnitude of an MR signal. For example, for T2 quantification, the extent of decay of an MR signal for each voxel in an MR image may be predicted from a plurality of images obtained at different echo times (TEs) by using an exponential decay equation.

A multi-echo acquisition method is mainly used in MRI for obtaining an actual T2 map, but T2 quantification from multiple echoes suffers from poor prediction accuracy and low reliability because the decay of an MR signal does not follow an exponential decay model due to incompleteness of a radio frequency (RF) pulse. To solve these problems, T2 quantification is performed using a Bloch equation or extended phase graphs (EPG) model. Recently, a method of performing T2 mapping by using an EPG Shinnar-Le Roux (EPG-SLR) model has been used. The EPG-SLR model is an MR signal modeling equation using RF slice profiles. However, quantification of a characteristic parameter via the MR signal modeling equation requires a long computation time.

SUMMARY

Provided are a magnetic resonance imaging (MRI) apparatus and a method of operating the same, and more particularly, an MRI apparatus and method whereby a characteristic parameter value may be acquired from MR signal data via training using an artificial neural network (ANN) and a parametric map may be generated based on the acquired characteristic parameter value.

Additional aspects will be set forth in part in the description which follows and, in part, will be apparent from the description, or may be learned by practice of the presented embodiments of the disclosure.

According to an embodiment of the disclosure, a method of generating a parametric map based on MR signal data includes: acquiring a trained network model by performing training in which MR signal data generated using a magnetic resonance imaging (MRI) method and an MR signal model is applied to an ANN as input and a first characteristic parameter value calculated via the MR signal model is applied to the ANN as groundtruth; and applying MR image data acquired by scanning an object to the trained network model to calculate a second characteristic parameter value with respect to the MR image data.

For example, the MR signal data may be an MR signal response simulated using a specific MR signal modeling equation according to an MR sequence for capturing an MR image of the object.

The MR signal modeling equation may be an equation for simulating the MR signal data by using the first characteristic parameter value and a radio frequency (RF) slice profile used for capturing the MR image of the object.

The MR signal data may include synthetic data that is a virtual MR signal response generated via simulation using an MR signal modeling equation and in-vivo MR image data pre-acquired with respect to the object, and the performing of the training may include performing the training by applying to the ANN at least one of the synthetic data or the pre-acquired in-vivo MR image data as input and the first characteristic parameter value as groundtruth.

The synthetic data may be an MR signal response simulated using a parameter value representing an extent of decay of the in-vivo MR image data at a specific echo time (TE) and an RF slice profile.

The performing of the training may include forming a pair of an input composed of the synthetic data and the pre-acquired in-vivo MR image data and a groundtruth that is the first characteristic parameter value corresponding to the input and performing the training by applying the pair to the ANN on a voxel-by-voxel basis.

The method may further include generating a parametric map based on the calculated second characteristic parameter value, and the parametric map may include at least one of a T1 map, a T2 map, a T1rho map, or a proton density (PD) map.

The method may further include displaying the parametric map.

The method may further include detecting an error by extracting a voxel at which a residual error value exceeds a preset threshold, wherein the residual error value is calculated for each voxel via the training.

The method may further include: creating a dictionary of the first characteristic parameter value in a preset range by using the MR signal model; acquiring from the dictionary the first characteristic parameter value corresponding to a voxel at which the error is detected; and correcting the error by replacing a value of the voxel at which the error is detected with the acquired first characteristic parameter value.

According to another embodiment of the disclosure, an MRI apparatus for generating a parametric map based on MR signal data includes: an RF coil configured to acquire, from at least one RF channel coil, an MR signal emitted from an object; a memory storing instructions for processing the MR signal received from the RF coil; and a processor configured to execute the stored instructions to: generate a trained network model by performing training in which MR signal data generated using an MRI method and an MR signal model is applied to an ANN as input and a first characteristic parameter value calculated via the MR signal model is applied to the ANN as groundtruth; and apply MR image data with respect to the object, which is generated by processing the MR signal, to the trained network model to calculate a second characteristic parameter value with respect to the MR image data.

The MR signal data may be an MR signal response simulated using a specific MR signal modeling equation according to an MR sequence for capturing an MR image of the object.

The MR signal modeling equation may be an equation for simulating the MR signal data by using the first characteristic parameter value and a RF slice profile used for capturing the MR image of the object.

The MR signal data may include synthetic data that is a virtual MR signal response generated via simulation using an MR signal modeling equation and in-vivo MR image data pre-acquired with respect to the object, and the processor may be further configured to execute the stored instructions to apply to the ANN at least one of the synthetic data or the pre-acquired in-vivo MR image data as input and the first characteristic parameter value as groundtruth.

The processor may be further configured to execute the stored instructions to generate the synthetic data via simulation using a parameter value representing an extent of decay of the in-vivo MR image data at a specific TE and a RF slice profile.

The processor may be further configured to execute the stored instructions to form a pair of an input composed of the synthetic data and the pre-acquired in-vivo MR image data and a groundtruth that is the first characteristic parameter value corresponding to the input and apply the pair to the ANN on a voxel-by-voxel basis.

The processor may be further configured to execute the stored instructions to generate a parametric map based on the calculated second characteristic parameter value, and the parametric map may include at least one of a T1 map, a T2 map, a T1rho map, or a PD map.

The MRI apparatus may further include a display, and the processor may be further configured to execute the stored instructions to control the display to display the parametric map.

The processor may be further configured to execute the stored instructions to detect an error for each voxel by extracting a voxel at which a residual error value exceeds a preset threshold, wherein the residual error value is calculated for each voxel via the training.

The processor may be further configured to execute the stored instructions to: create a dictionary of the first characteristic parameter value in a preset range by using the MR signal model; acquire from the dictionary the first characteristic parameter value corresponding to a voxel at which the error is detected; and correct the error by replacing a value of the voxel at which the error is detected with the acquired first characteristic parameter value.

According to another embodiment of the disclosure, a computer program product includes a computer-readable storage medium, wherein the computer-readable storage medium includes instructions for: acquiring a trained network model by performing training in which MR signal data generated using an MRI method and an MR signal model is applied to an ANN as input and a first characteristic parameter value calculated via the MR signal model is applied to the ANN as groundtruth; and applying MR image data acquired by scanning an object to the trained network model to calculate a second characteristic parameter value with respect to the MR image data.

Embodiments provided herein include a method of generating a parametric map based on magnetic resonance (MR) signal data. The method including: acquiring a trained network model, wherein the acquiring comprises performing training of an artificial neural network on MR signal data, wherein the MR signal data is generated using a magnetic resonance imaging (MRI) method and wherein the MRI method is based on an MR signal model, and wherein the performing training comprises applying, as a ground truth to the artificial neural network, a first characteristic parameter value calculated via the MR signal model; acquiring MR image data by scanning an object; applying the MR image data to the trained network model; and calculating, using the trained network model and based on the MR image data, a second characteristic parameter value with respect to the MR image data.

In some embodiments, the MR signal data is an MR signal response simulated using an MR signal modeling equation, and wherein the MR signal modeling equation is based on an MR sequence for capturing an MR image of the object.

In some embodiments, the MR signal modeling equation is an equation for simulating the MR signal data, wherein the MR signal modeling equation is based on the first characteristic parameter value and a radio frequency slice profile, and wherein the acquiring the MR image data comprises using the radio frequency slice profile.

In some embodiments, the MR signal data comprises synthetic data, and wherein the synthetic data includes a virtual MR signal response, wherein the virtual MR signal response is generated via simulation based on an MR signal modeling equation and based on in-vivo MR image data pre-acquired with respect to the object, wherein the performing training comprises performing training on the pre-acquired in-vivo MR image data.

In some embodiments, the synthetic data is based on an MR signal response, wherein the MR signal response is obtained by a simulation using a parameter value representing an extent of decay of the in-vivo MR image data at a specific echo time (TE) and based on a radio frequency slice profile.

In some embodiments, the performing training includes: associating as a pair: i) the synthetic data and the pre-acquired in-vivo MR image data, and ii) the groundtruth; and applying the pair to the artificial neural network on a voxel-by-voxel basis with respect to the in-vivo MR image data.

In some embodiments, the method also includes generating a parametric map based on the calculated second characteristic parameter value, wherein the parametric map comprises at least one of a T1 map, a T2 map, a T1rho map, or a proton density (PD) map.

In some embodiments, the method also includes displaying the parametric map.

In some embodiments, the method also includes calculating, based on the training, a residual error value for a voxel of a plurality of voxels; and detecting an error by extracting the voxel based on the residual error value exceeding a preset threshold, wherein the parametric map includes the plurality of voxels.

In some embodiments, the method also includes creating a dictionary of the first characteristic parameter value in a preset range by using the MR signal model; acquiring from the dictionary the first characteristic parameter value corresponding to the voxel at which the error is detected; and correcting the error by replacing a value of the voxel at which the error is detected with the acquired first characteristic parameter value.

Also disclosed herein is a magnetic resonance imaging (MRI) apparatus for generating a parametric map based on magnetic resonance (MR) signal data. The apparatus includes: a radio frequency coil configured to acquire, from at least one radio frequency channel coil, an MR signal emitted from an object; a memory storing instructions for processing the MR signal received from the radio frequency coil; and a processor configured to execute the stored instructions to: generate a trained network model by performing training of an artificial neural network on MR signal data, wherein the MR signal data is generated using an MRI method and wherein the MRI method is based on an MR signal model, and wherein the performing training comprises applying, as a ground truth to the artificial neural network, a first characteristic parameter value calculated based on the MR signal model; acquire MR image data by scanning an object; apply the MR image data to the trained network model; and calculate, using the trained network model and based on the MR image data, a second characteristic parameter value with respect to the MR image data.

In some embodiments of the MRI apparatus, the MR signal data is an MR signal response simulated using an MR signal modeling equation, and wherein the MR signal modeling equation is based on an MR sequence for capturing an MR image of the object.

In some embodiments of the MRI apparatus, the MR signal modeling equation is an equation for simulating the MR signal data, wherein the MR signal modeling equation is based on the first characteristic parameter value and a radio frequency slice profile, wherein the acquiring the MR image data comprises using the radio frequency slice profile.

In some embodiments of the MRI apparatus, the MR signal data comprises synthetic data, and wherein the synthetic data includes a virtual MR signal response, wherein the virtual MR signal response is generated via simulation based on an MR signal modeling equation and based on in-vivo MR image data pre-acquired with respect to the object, and wherein the processor is further configured to execute the stored instructions to generate a trained network model by performing training on the pre-acquired in-vivo MR image data.

In some embodiments of the MRI apparatus, the processor is further configured to execute the stored instructions to generate the synthetic data based on a parameter value representing an extent of decay of the in-vivo MR image data at a specific echo time (TE) and based on a radio frequency slice profile.

In some embodiments of the MRI apparatus, the processor is further configured to execute the stored instructions to: associate as a pair: i) the synthetic data and the pre-acquired in-vivo MR image data, and ii) the groundtruth; and generate a trained network model by performing the training by applying the pair to the artificial neural network on a voxel-by-voxel basis with respect to the in-vivo MR image data.

In some embodiments of the MRI apparatus, the processor is further configured to execute the stored instructions to generate a parametric map based on the calculated second characteristic parameter value, and wherein the parametric map comprises at least one of a T1 map, a T2 map, a T1rho map, or a proton density (PD) map.

In some embodiments of the MRI apparatus, the MRI apparatus includes a display, wherein the processor is further configured to execute the stored instructions to control the display to display the parametric map.

In some embodiments of the MRI apparatus, the processor is further configured to execute the stored instructions to: calculate, based on the training, a residual error value for a voxel of a plurality of voxels; and detect an error for the voxel by extracting the voxel, wherein the residual error value exceeds a preset threshold, wherein the parametric map includes the plurality of voxels.

In some embodiments of the MRI apparatus, the processor is further configured to execute the stored instructions to: create a dictionary of the first characteristic parameter value in a preset range by using the MR signal model; acquire from the dictionary the first characteristic parameter value corresponding to the voxel at which the error is detected; and correct the error by replacing a value of the voxel at which the error is detected with the acquired first characteristic parameter value.

Also disclosed herein is a computer program product comprising a non-transitory computer-readable storage medium, wherein the non-transitory computer-readable storage medium comprises instructions for performing a method of operating a magnetic resonance imaging (MRI) apparatus, the method comprising: acquiring a trained network model, wherein the acquiring comprises performing training of an artificial neural network on magnetic resonance (MR) signal data, wherein the MR signal data is generated using an MRI method and wherein the MRI method is based on an MR signal model, and wherein the performing training comprises applying, as a ground truth to the artificial neural network, a first characteristic parameter value calculated via the MR signal model; acquiring MR image data by scanning an object; applying the MR image data to the trained network model; and calculating, using the trained network model and based on the MR image data, a second characteristic parameter value with respect to the MR image data.

BRIEF DESCRIPTION OF THE DRAWINGS

The above and other aspects, features, and advantages of certain embodiments of the disclosure will be more apparent from the following description taken in conjunction with the accompanying drawings, in which:

FIG. 7 illustrates an example in which an MRI apparatus corrects an error by using a dictionary of a characteristic parameter, according to an embodiment of the disclosure;

FIG. 8 is a flowchart of a method, performed by an MRI apparatus, of correcting an error by using a dictionary of a characteristic parameter, according to an embodiment of the disclosure;

DETAILED DESCRIPTION

Figure 1:
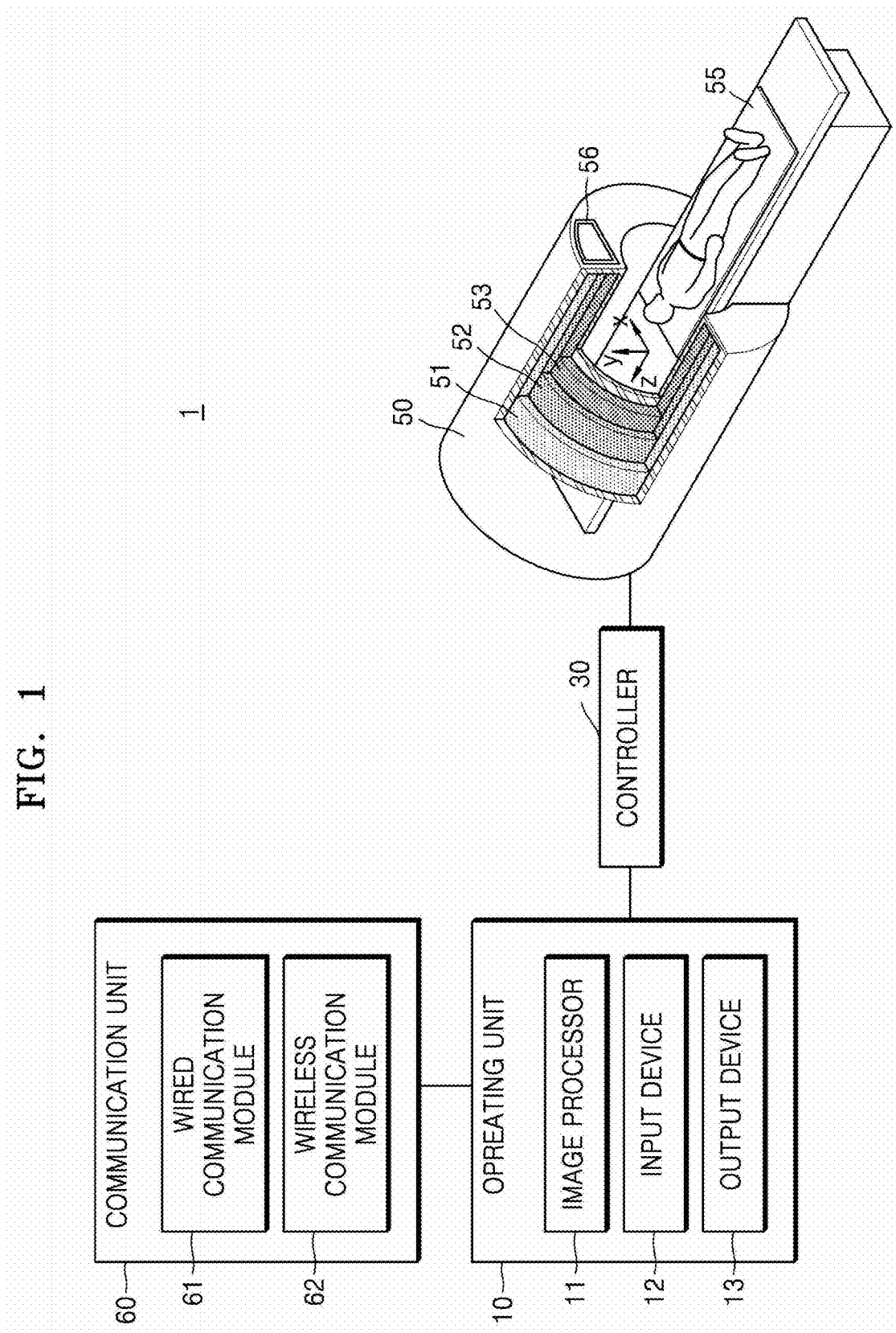
FIG. 1 illustrates components of a magnetic resonance imaging (MRI) system.

The present specification describes principles of the disclosure and sets forth embodiments thereof to clarify the scope of the disclosure and to allow those of ordinary skill in the art to implement the embodiments. The present embodiments may have different forms.

Like reference numerals refer to like elements throughout. The present specification does not describe all components in the embodiments, and common knowledge in the art or the same descriptions of the embodiments will be omitted below. The term "part" or "portion" may be implemented using hardware or software, and according to embodiments, one "part" or "portion" may be formed as a single unit or element or include a plurality of units or elements. Hereinafter, the principles and embodiments of the disclosure will be described in detail with reference to the accompanying drawings.

In the present specification, an "object" may be a target to be imaged and include a human, an animal, or a part of a human or animal. For example, the object may include a body part (an organ) or a phantom.

Throughout the disclosure, the expression "at least one of a, b or c" indicates only a, only b, only c, both a and b, both a and c, both b and c, all of a, b, and c, or variations thereof.

An MRI system acquires an MR signal and reconstructs the acquired MR signal into an image. The MR signal denotes a radio frequency (RF) signal emitted from the object.

In the MRI system, a main magnet creates a static magnetic field to align a magnetic dipole moment of a specific atomic nucleus of the object placed in the static magnetic field along a direction of the static magnetic field. A gradient coil may generate a gradient magnetic field by applying a gradient signal to a static magnetic field and induce resonance frequencies differently according to each region of the object.

An RF coil may emit an RF signal to match a resonance frequency of a region of the object whose image is to be acquired. Furthermore, when gradient magnetic fields are applied, the RF coil may receive MR signals having different resonance frequencies emitted from a plurality of regions of the object. Though this process, the MRI system may obtain an image from an MR signal by using an image reconstruction technique.

Additional description is provided in "Artificial Neural Network for Real-Time T2 Mapping with Quality Assurance," by Doohee Lee et al., published at ISMRM on Jun. 1, 2018, the contents of which are hereby incorporated by reference herein.

FIG. 1 is a schematic diagram of an MRI system 1.

Referring to FIG. 1, the MRI system 1 may include an operating unit 10, a controller 30, and a scanner 50. The controller 30 may be independently separated from the operating unit 10 and the scanner 50. Furthermore, the controller 30 may be separated into a plurality of sub-components and incorporated into the operating unit 10 and the scanner 50 in the MRI system 1. Operations of the components in the MRI system 1 will now be described in detail.

The scanner 50 may be formed to have a cylindrical shape (e.g., a shape of a bore) having an empty inner space into which an object may be inserted. A static magnetic field and a gradient magnetic field are created in the inner space of the scanner 50, and an RF signal is emitted toward the inner space.

The scanner 50 may include a static magnetic field generator 51, a gradient magnetic field generator 52, an RF coil unit 53, a table 55, and a display 56. The static magnetic field generator 51 creates a static magnetic field for aligning magnetic dipole moments of atomic nuclei of the object in a direction of the static magnetic field. The static magnetic field generator 51 may be formed as a permanent magnet or superconducting magnet using a cooling coil.

The gradient magnetic field generator 52 is connected to the controller 30 and generates a gradient magnetic field by applying a gradient to a static magnetic field in response to a control signal received from the controller 30. The gradient magnetic field generator 52 includes X, Y, and Z coils for generating gradient magnetic fields in X-, Y-, and Z-axis directions crossing each other at right angles and generates a gradient signal according to a position of a region being imaged so as to differently induce resonance frequencies according to regions of the object.

The RF coil unit 53 connected to the controller 30 may emit an RF signal toward the object in response to a control signal received from the controller 30 and receive an MR signal emitted from the object. In detail, the RF coil unit 53 may transmit, toward atomic nuclei of the object having precessional motion, an RF signal having the same frequency as that of the precessional motion, stop transmitting the RF signal, and then receive an MR signal emitted from the object.

The RF coil unit 53 may be formed as a transmitting RF coil for generating an electromagnetic wave having an RF corresponding to the type of an atomic nucleus, a receiving RF coil for receiving an electromagnetic wave emitted from an atomic nucleus, or one transmitting/receiving RF coil serving both functions of the transmitting RF coil and receiving RF coil. Furthermore, in addition to the RF coil unit 53, a separate coil may be attached to the object. Examples of the separate coil may include a head coil, a spine coil, a torso coil, and a knee coil according to a region being imaged or to which the separate coil is attached.

The display 56 may be disposed outside and/or inside the scanner 50. The display 56 is also controlled by the controller 30 to provide a user or the object with information related to medical imaging.

Furthermore, the scanner 50 may include an object monitoring information acquisition unit (not shown) configured to acquire and transmit monitoring information about a state of the object. For example, the object monitoring information acquisition unit may acquire monitoring information related to the object from a camera (not shown) for capturing images of a movement or position of the object, a respiration measurer (not shown) for measuring the respiration of the object, an ECG measurer for measuring the electrical activity of the heart, or a temperature measurer for measuring a temperature of the object and transmit the acquired monitoring information to the controller 30. The controller 30 may in turn control an operation of the scanner 50 based on the monitoring information. Operations of the controller 30 will now be described in more detail.

The controller 30 may control overall operations of the scanner 50.

The controller 30 may control a sequence of signals formed in the scanner 50. The controller 30 may control the gradient magnetic field generator 52 and the RF coil unit 53 according to a pulse sequence received from the operating unit 10 or a designed pulse sequence.

A pulse sequence may include all pieces of information required to control the gradient magnetic field generator 52 and the RF coil unit 53. For example, the pulse sequence may include information about a strength, a duration, and application timing of a pulse signal applied to the gradient magnetic field generator 52.

The controller 30 may control a waveform generator (not shown) for generating a gradient wave, i.e., an electrical pulse according to a pulse sequence and a gradient amplifier (not shown) for amplifying the generated electrical pulse and transmitting the same to the gradient magnetic field generator 52. Thus, the controller 30 may control formation of a gradient magnetic field by the gradient magnetic field generator 52.

Furthermore, the controller 30 may control an operation of the RF coil unit 53. For example, the controller 30 may supply an RF pulse having a resonance frequency to the RF coil unit 30 that emits an RF signal toward the object, and receive an MR signal received by the RF control unit 53. In this case, the controller 30 may adjust emission of an RF signal and reception of an MR signal according to an operating mode by controlling an operation of a switch (e.g., a T/R switch) for adjusting transmitting and receiving directions of the RF signal and the MR signal based on a control signal.

The controller 30 may control a movement of the table 55 where the object is placed. Before MRI is performed, the controller 30 may move the table 55 according to which region of the object is to be imaged.

The controller 30 may also control the display 56. For example, the controller 30 control the on/off state of the display 56 or a screen to be output on the display 56 according to a control signal.

The controller 30 may be formed as an algorithm for controlling operations of the components in the MRI system 1, a memory (not shown) for storing data in the form of a program, and a processor for performing the above-described operations by using the data stored in the memory. In this case, the memory and the processor may be implemented as separate chips. Alternatively, the memory and processor may be incorporated into a single chip.

The operating unit 10 may control overall operations of the MRI system 1 and include an image processing unit 11, an input device 12, and an output device 13.

The image processing unit 11 may control the memory to store an MR signal received from the controller 30, and generate image data with respect to the object from the stored MR signal by applying an image reconstruction technique by using an image processor.

For example, when a k space (for example, also referred to as a Fourier space or a frequency space) of the memory is filled with digital data to complete k-space data, the image processing unit 11 may reconstruct image data from the k-space data by applying various image reconstruction techniques (e.g., by performing inverse Fourier transform on the k-space data) by using the image processor.

Furthermore, the image processing unit 11 may perform various signal processing operations on MR signals in parallel. For example, image processing unit 11 may perform signal processing on a plurality of MR signals received via a multi-channel RF coil in parallel so as to convert the plurality MR signals into image data. In addition, the image processing unit 11 may store not only the image data in the memory, or the controller 30 may store the same in an external server via a communication unit 60 as will be described below.

The input device 12 may receive, from the user, a control command for controlling the overall operations of the MRI system 1. For example, the input device 12 may receive, from the user, object information, parameter information, a scan condition, and information about a pulse sequence. The input device 12 may be a keyboard, a mouse, a track ball, a voice recognizer, a gesture recognizer, a touch screen, or any other input device.

The output device 13 may output image data generated by the image processing unit 11. The output device 13 may also output a user interface (UI) configured so that the user may input a control command related to the MRI system 1. The output device 13 may be formed as a speaker, a printer, a display, or any other output device.

Furthermore, although FIG. 1 shows that the operating unit 10 and the controller 30 are separate components, the operating unit 10 and the controller 30 may be included in a single device as described above. Furthermore, processes respectively performed by the operating unit 10 and the controller 30 may be performed by another component. For example, the image processing unit 11 may convert an MR signal received from the controller 30 into a digital signal, or the controller 30 may directly perform the conversion of the MR signal into the digital signal.

The MRI system 1 may further include a communication unit 60 and be connected to an external device (not shown) such as a server, a medical apparatus, and a portable device (e.g., a smartphone, a tablet PC, a wearable device, etc.) via the communication unit 60.

The communication unit 60 may include at least one component that enables communication with an external device. For example, the communication unit 60 may include at least one of a local area communication module (not shown), a wired communication module 61, or a wireless communication module 62.

The communication unit 60 may receive a control signal and data from an external device and transmit the received control signal to the controller 30 so that the controller 30 may control the MRI system 1 according to the received signal.

Alternatively, by transmitting a control signal to an external device via the communication unit 60, the controller 30 may control the external device according to the control signal.

For example, the external device may process data of the external device according to a control signal received from the controller 30 via the communication unit 60.

A program for controlling the MRI system 1 may be installed on the external device and may include instructions for performing some or all of the operations of the controller 30.

The program may be preinstalled on the external device, or a user of the external device may download the program from a server providing an application for installation. The server providing an application may include a recording medium having the program recorded thereon.

Figure 2:
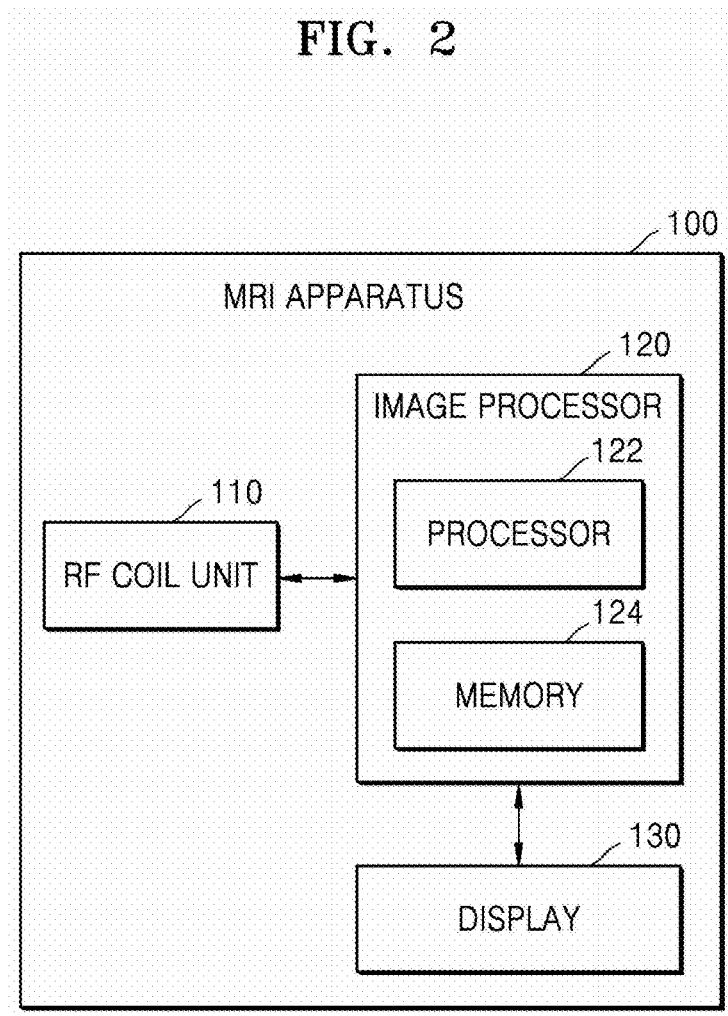
FIG. 2 is a block diagram illustrating components of an MRI apparatus according to an embodiment of the disclosure.
Figure 3:
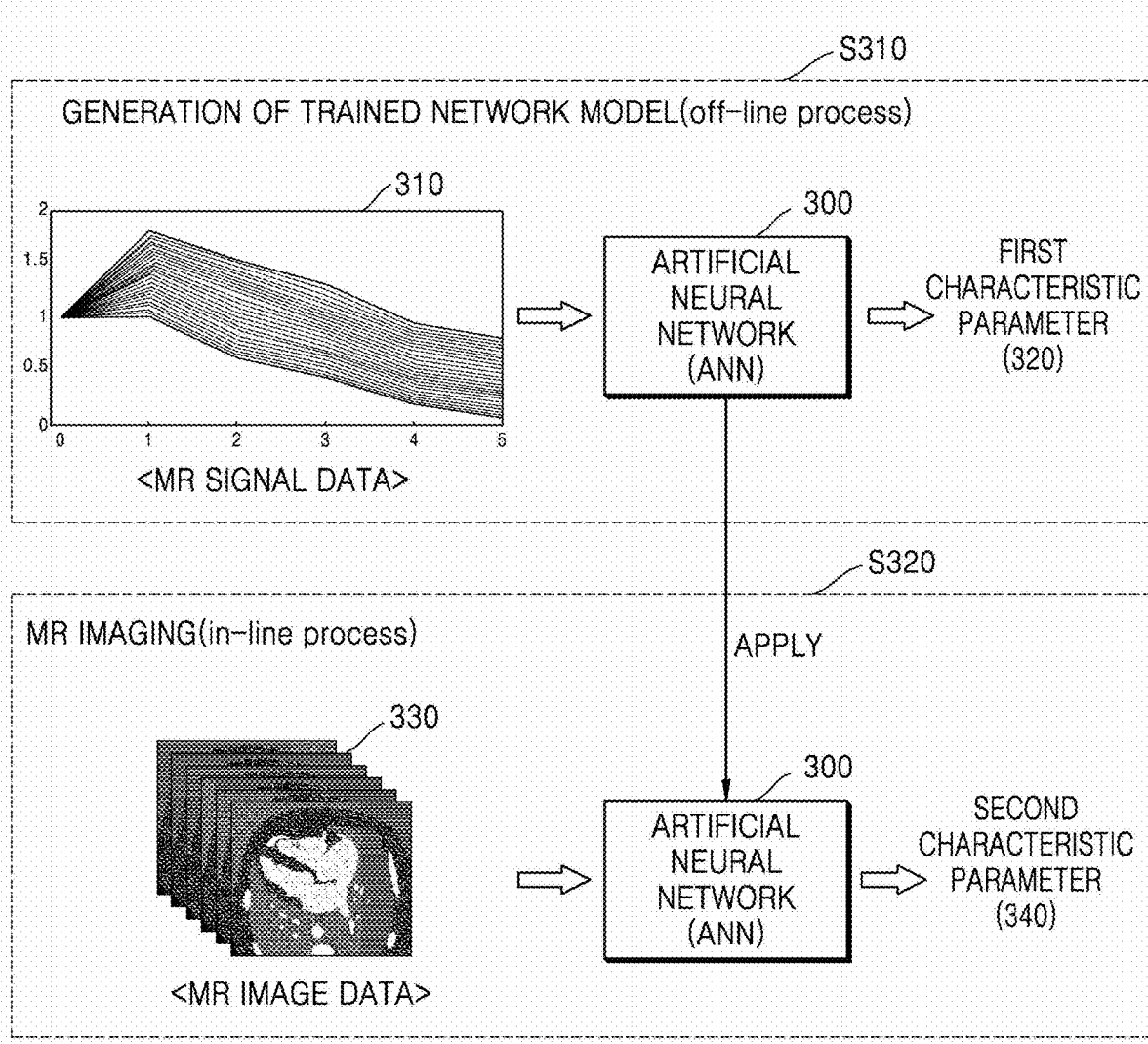
FIG. 3 is a conceptual diagram illustrating a method, performed by an MRI apparatus, of performing training using MR signal data and a first characteristic parameter value and calculating a second characteristic parameter from MR image data with respect to an object by applying a network model acquired via the training, according to an embodiment of the disclosure.

FIG. 2 is a block diagram illustrating components of an MRI apparatus 100, and FIG. 3 is a conceptual diagram illustrating a method, performed by the MRI apparatus 100, of performing training with MR signal data and a first characteristic parameter value and calculating a second characteristic parameter from MR image data with respect to an object by applying a network model acquired via the training, according to an embodiment of the disclosure. Referring to FIG. 2, the MRI apparatus 100 may include an RF coil unit 110, an image processor 120, and a display 130. FIG. 2 shows only essential components of the MRI apparatus 100, and thus the MRI apparatus 100 may not include only the components shown in FIG. 2. According to an embodiment of the disclosure, the MRI apparatus 100 may be the same as the MRI system 1 of FIG. 1 or may further include the components described with reference to FIG. 1.

The RF coil unit 110 may emit an RF signal toward the object and receive an MR signal emitted from the object. In detail, the RF coil unit 110 may transmit, toward atomic nuclei of the object performing a precessional motion, an RF signal having the same frequency as that of the precessional motion, stop transmitting the RF signal, and then receive an MR signal emitted from the object. According to an embodiment of the disclosure, the RF coil unit 110 may be formed as a transmitting/receiving RF coil serving both transmit and receive functions. Because the RF coil unit 110 corresponds to the RF coil unit 53 of FIG. 1, descriptions that are already provided above with respect to FIG. 1 will be omitted here.

The image processor 120 may be a component that receives the MR signal received by the RF coil unit 110 from the object and performs various types of signal processing, such as amplification, frequency transformation, phase detection, low frequency amplification, filtering, etc., on the received MR signal to generate MR image data with respect to the object. The image processor 120 may include a processor 122 and a memory 124. According to an embodiment of the disclosure, the image processor 120 may include the memory 124 that stores program code, instructions, or data for performing operations of processing an MR signal and the processor 122 that processes the program code, instructions, or data stored in the memory 124. Although not shown in FIG. 2, the image processor 120 may further include an artificial intelligence (AI) learning module.

The image processor 120 is implementable as various combinations of at least one processor 124 and at least one processor 120. The processor 122 may generate and delete a program module according to an operation state of the MRI apparatus 100 and process operations of the program module. According to an embodiment of the disclosure, the image processor 120 may be implemented as a hardware component such as a field-programmable gate array (FPGA) or an application-specific integrated circuit (ASIC). However, embodiments of the disclosure are not limited thereto, and the image processor 120 may include components such as software components, object-oriented software components, class components and task components, processes, functions, attributes, procedures, subroutines, segments of program code, drivers, firmware, micro codes, circuits, data, a database, data structures, tables, arrays, and variables.

The processor 122 of the image processor 120 may be composed of a hardware device having computational capabilities of performing commonly used image processing techniques or machine learning algorithms. For example, the image processor 120 may be composed of a hardware module including at least one of a central processing unit (CPU), a microprocessor, or a graphics processing unit. According to an embodiment of the disclosure, the processor 122 may also be composed of an application processor (AP).

The memory 124 is a hardware device capable of storing program code or data for performing functions of the MRI apparatus 100, and may be composed of random access memory (RAM) or read-only memory (ROM) but is not limited thereto. According to an embodiment of the disclosure, the memory 124 and the processor 122 may be implemented as separate chips. Alternatively, the memory 124 and the processor 122 may be incorporated into a single chip.

The processor 122 may acquire a trained network model via training during which MR signal data generated using an MRI method and an MR signal model is applied to an artificial neural network (ANN) as input and a first characteristic parameter value calculated via the MR signal model is applied thereto as groundtruth. In this case, the MR signal model is a modeling equation used according to a method of acquiring MR image data with respect to an object, i.e., an imaging modality, and may be an equation for simulating the extent of decay of an MR signal. MR signal data may be an MR signal response simulated using a specific MR signal modeling equation according to an MR sequence for capturing an MR image of the object. According to an embodiment of the disclosure, MR signal data may be composed of one of synthetic data that is a virtual MR signal response generated via simulation using an MR signal modeling equation, in-vivo MR image data pre-acquired with respect to the object, and a combination of the synthetic data and the in-vivo MR image data.

Referring to FIGS. 2 and 3, the processor 122 may acquire a trained network model via training during which MR signal data 310 is applied to an ANN 300 as input and a first characteristic parameter 320 calculated via an MR signal model is applied to the ANN 300 as groundtruth. In this case, a value of the first characteristic parameter 320 corresponding to the groundtruth may be a characteristic parameter value calculated using a Bloch equation, an Extended Phase Graphs (EPG) modeling equation, an EPG Shinnar-Le Roux (EPG-SLR) modeling equation, or a known curve fitting modeling equation. For example, when an exponential decay is used in T2 mapping, a groundtruth of the ANN 300 may be a T2 time value. When EPG-SLR modelling is used in T2 mapping, a groundtruth of the ANN 300 may be an E2 value (an exponential value at T2 time) and a B1 value.

The ANN 300 may include a known deep neural network (DNN) such as Convolution Neural Network (CNN) or Recurrent Neural Network (RNN). However, the processor 122 may perform training by using algorithms such as support vector machine (SVM), linear regression, logistic regression, Naïve Bayes, decision tree, k-nearest neighbor (kNN) algorithm, etc. In this case, the training may be performed by a separate AI learning module. According to an embodiment of the disclosure, the processor 122 and the AI learning module may be integrated into a single chip.

According to an embodiment of the disclosure, the processor 122 may form an input/output pair including an input consisting of synthetic data and in-vivo MR image data and a first characteristic parameter value corresponding to the input and perform training by applying the formed input/output pair to the ANN 300 on a voxel-by-voxel basis. According to an embodiment of the disclosure, the processor 122 may form a pair consisting of at least one of synthetic data or in-vivo MR image data as an input and a first characteristic parameter as a groundtruth and perform training by applying the formed pair to the ANN 300 on a voxel-by-voxel basis.

The processor 122 acquires a trained network model via the training, and the process of acquiring the trained network model may be an off-line process (S310) performed prior to MR imaging of the object.

The processor 122 may calculate a second characteristic parameter 340 by applying MR image data 330 acquired by scanning the object to the trained network model acquired via the training. The process of calculating the second characteristic parameter 340 may be an in-line process (S320) performed by the processor 122 together with the MR imaging of the object.

A method by which the processor 122 performs off-line training by using an ANN and performs an in-line process for applying a trained network model to MR image data with respect to the object to calculate a second characteristic parameter will be described in more detail below with reference to FIGS. 6A and 6B.

The processor 122 may generate a parametric map by mapping the second characteristic parameter value 340 calculated via the training on a voxel-by-voxel basis. For example, the parametric map may include at least one of a T1 map, a T2 map, a T1rho map, or a proton density (PD) map.

Referring to FIG. 2, the processor 122 may generate synthetic data that is a virtual MR signal response by performing simulation using an MR signal modeling equation. In this case, the MR signal response means an intensity of an MR signal with respect to time. For example, the MR signal response may be the extent of spin relaxation, i.e., the extent of decay of an MR signal, across a plurality of echo times (TEs). To quantify a magnitude of an MR signal response, characteristic parameters for quantifying characteristics of the object, i.e., tissue, with respect to a plurality of TEs may be used. The characteristic parameters may be T1, T2, T1rho, PD, etc. To quantify the extent of decay of an MR signal intensity with respect to a plurality of TEs, the processor 122 may perform parametric mapping by using at least one of a T1 map, a T2 map, a T1 rho map, or a PD map.

According to an embodiment of the disclosure, to obtain a T2 map, the processor 122 may simulate an MR signal response from a multi-spin-echo (MSE) sequence by using an exponential decay model. However, in general, decay of an MR signal from a MSE sequence is not accurately predicted with an exponential decay model due to inhomogeneity of RF pulses. According to an embodiment of the disclosure, the processor 122 may simulate the extent of decay of an MR signal from a MSE sequence by using at least one of Bloch equation-based modeling, EPG-based signal modeling, or EPG-SLR modeling equation and generate synthetic data via the simulation. However, embodiments of the disclosure are not limited thereto, and the processor 122 may simulate an MR signal response by using any known curve fitting modeling method to generate synthetic data.

According to an embodiment of the disclosure, the processor 122 may simulate an MR signal response by using an EPG-SLR modeling equation that takes into account RF slice profiles used for capturing an MR image of the object and then generate synthetic data, as described in more detail below with reference to FIG. 5B.

The processor 122 may calculate a residual error value at each voxel via training and detect an error for each voxel by extracting a voxel at which the calculated residual error value exceeds a preset threshold. According to an embodiment of the disclosure, the processor 122 may create a dictionary of characteristic parameter values in a preset range by using an MR signal modeling equation and correct an error by replacing a value of a voxel at which an error is detected with a characteristic parameter value of a corresponding voxel in the dictionary. A method, performed by the processor 122, of detecting an error for each voxel and correcting the detected error will be described in more detail below with reference to FIGS. 7 and 8.

The display 130 may display a parametric map generated by the image processor 120. For example, the display 130 may be constituted by a physical device including at least one of a liquid crystal display (LCD), a plasma display panel (PDP), an organic light-emitting display (OLED), a field emission display (FED), a light-emitting diode (LED) display, a vacuum fluorescent display (VFD), a digital light processing (DLP) display, a flat panel display (FPD), a three-dimensional (3D) display, or a transparent display, but is not limited thereto. According to an embodiment of the disclosure, the display 130 may be formed as a touch screen including a touch interface.

Figure 4:
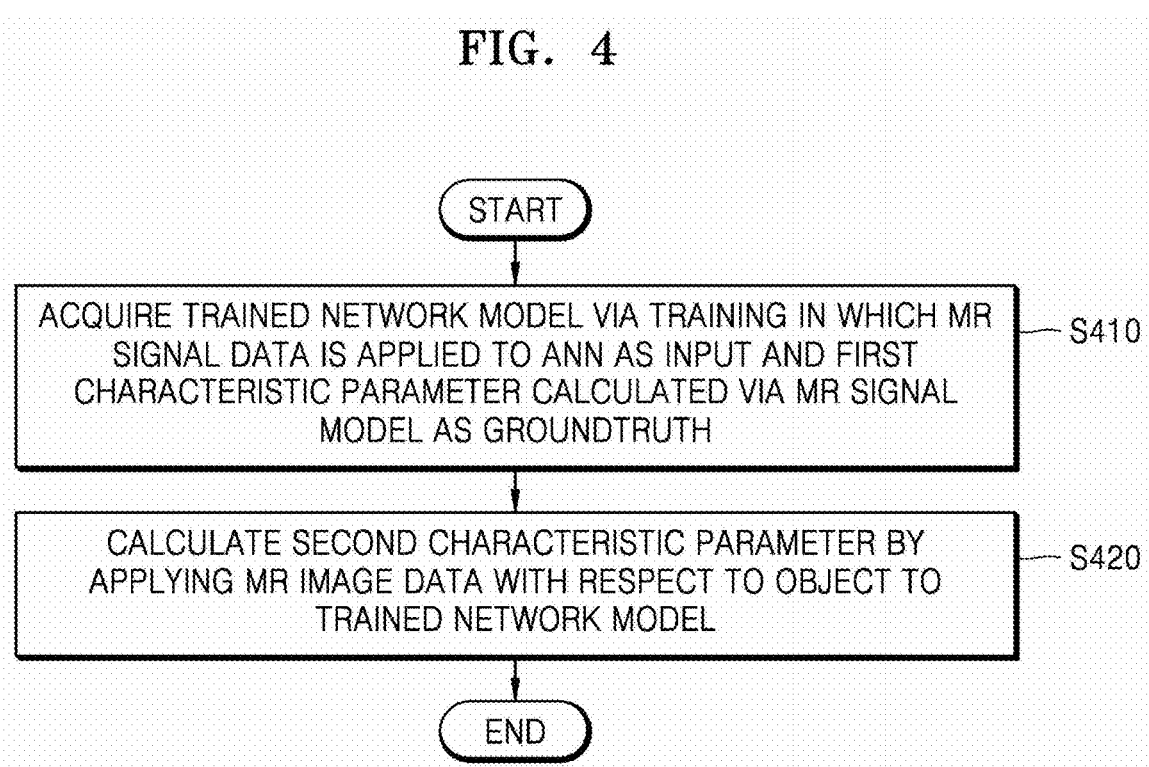
FIG. 4 is a flowchart of a method of operating an MRI apparatus, according to an embodiment of the disclosure.

FIG. 4 is a flowchart of a method of operating an MRI apparatus, according to an embodiment of the disclosure.

The MRI apparatus acquires a trained network model via training in which MR signal data is applied to an ANN as input and a first characteristic parameter value calculated via an MR signal model is applied thereto as groundtruth (S410). In this case, MR signal data may consist of one of synthetic data that is a virtual MR signal response generated via simulation using an MR signal modeling equation, in-vivo MR image data pre-acquired with respect to an object, or a combination of the synthetic data and the in-vivo MR image data.

According to an embodiment of the disclosure, the MRI apparatus may perform training by using a known DNN such as CNN or RNN. However, embodiments of the disclosure are not limited thereto, and the MRI apparatus may also perform training by using algorithms such as SVM, linear regression, logistic regression, Naïve Bayes, decision tree, kNN algorithm, etc.

According to an embodiment of the disclosure, the MRI apparatus may generate synthetic data via simulation using an MR signal modeling equation. The generated synthetic data may be data obtained by processing an MR signal response representing an intensity of an MR signal with respect to time. According to an embodiment of the disclosure, the MRI apparatus may simulate an MR signal response from a MSE sequence by using at least one of an exponential decay model, Bloch equation-based modeling, EPG-based signal modeling, or an EPG-SLR modeling equation and generate synthetic data via the simulation. However, embodiments of the disclosure are not limited thereto, and the MRI apparatus may simulate an MR signal response by using any known curve fitting modeling method and generate synthetic data.

According to an embodiment of the disclosure, the MRI apparatus may simulate an MR signal response by using an EPG-SLR modeling equation that takes into RF slice profiles used for capturing an MR image of the object and then generate the synthetic data.

According to an embodiment of the disclosure, the MRI apparatus may form an input/output pair including an input consisting of at least one of synthetic data generated via simulation or in-vivo MR image data pre-acquired with respect to the object and a first characteristic parameter that is a groundtruth corresponding to the input and perform training by applying the formed input/output pair to the ANN on a voxel-by-voxel basis.

The MRI apparatus calculates a second characteristic parameter by applying MR image data with respect to the object to the trained network model acquired via the training in operation S410 (S420). For example, when performing T2 mapping, the MRI apparatus may apply MR image data acquired by performing MR imaging on the object to a trained network model as input to calculate an E2 value (an exponential value at T2 time) and a B1 value. Operation S420 may be an in-line process performed together with MR imaging of the object. Operation S420 may include the process of capturing an MR image of the object, and the MR image data applied as input in operation S420 may be different from the MR signal data pre-acquired in operation S410.

According to an embodiment of the disclosure, the MRI apparatus may generate a parametric map based on the calculated characteristic parameter. For example, the MRI apparatus may generate at least one parametric map from among a T1 map, a T2 map, a T1rho map, or a PD map.

According to the related art, an exponential decay model or a modeling method using a Bloch equation has been used as a parametric mapping method for quantifying an MR signal response. However, decay of an MR signal from a MSE sequence does not follow an exponential decay model due to imperfect RF pulses. To solve the problem, an EPG model or EPG-SLR model may be used for parametric mapping. However, parametric mapping using an EPG or EPG-SLR model may achieve a high degree of prediction accuracy but require a very long computation time.

According to the embodiments of the disclosure described with reference to FIGS. 2 through 4, the MRI apparatus may perform training by applying MR signal data and a first characteristic parameter value to an ANN, calculate a second characteristic parameter value by using a trained network model together with MR imaging of the object, and generate a parametric map based on the calculated characteristic parameter value. Thus, it is possible to significantly reduce the computation time required to perform parametric mapping. Furthermore, according to an embodiment of the disclosure, the MRI apparatus may perform a training process via an ANN that takes at least one of virtual synthetic data generated using a simulation modeling equation or pre-acquired MR image data with respect to the object as input and a first characteristic parameter value as groundtruth. Thus, it is possible to provide a parametric mapping method with improved accuracy.

Furthermore, a training process via an ANN involves performing an off-line process prior to MR imaging of an actual object and performing a process (an in-line process) for applying MR image data acquired during the MR imaging of the actual object to a trained network model acquired during the off-line process, thereby reducing the computation time required for parametric mapping. Improvement of prediction accuracy and reduction of the computation time according to the embodiments of the disclosure described with reference to FIGS. 2 through 4 will be described in more detail below with reference to FIGS. 9 and 10.

Figure 5A:
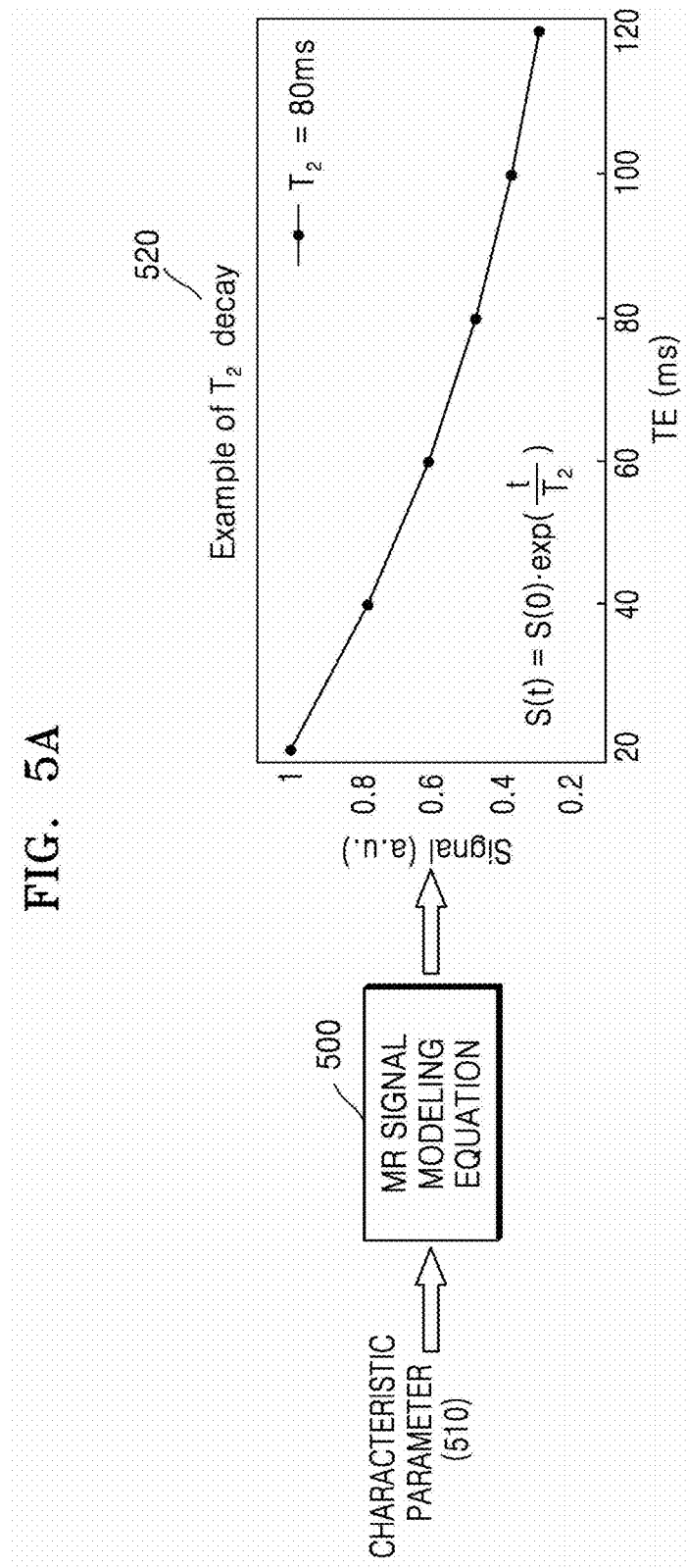
FIG. 5A illustrates an example in which an MR signal response is generated based on a characteristic parameter by using an MR signal modeling equation, according to an embodiment of the disclosure.

FIG. 5A illustrates an example in which an MR signal response is generated based on a characteristic parameter 510 by using an MR signal modeling equation 500, according to an embodiment of the disclosure.

Referring to FIG. 5A, an MRI apparatus may simulate an MR signal response 520 by applying the characteristic parameter 510 to the MR signal modeling equation 500. In this case, for example, the characteristic parameter 510 may include at least one of T1, T2, T1rho, or PD. The MR signal response 520 is represented by a curve of spin relaxation rates against a plurality of TEs and may mean the extent of decay of an MR signal magnitude.

The MRI apparatus may use a different MR signal modeling equation 500 according to a method of capturing an MR image. According to the embodiment of the disclosure shown in FIG. 5A, the MRI apparatus may generate the MR signal response 520 by using an exponential decay curve for T2 mapping as shown in Equation (1) below:

$$S(t) = S(0) \times \exp\left(-\frac{t}{T2}\right) \tag{1}$$

Although FIG. 5A illustrates an example in which the MR signal response 520 is generated using the exponential decay curve, embodiments of the disclosure are not limited thereto. According to an embodiment of the disclosure, the MRI apparatus may generate an MR signal response by using a Bloch equation or known curve fitting modeling equation.

However, because T2 mapping using a MSE sequence does not take into account an RF slice profile used in MR imaging, a calculated T2 value may vary depending on a state of an RF pulse applied to the MRI apparatus. In particular, an exponential decay model provides poor prediction accuracy for T2 mapping and thus has not been recognized as a reliable modeling tool for users.

Figure 5B:
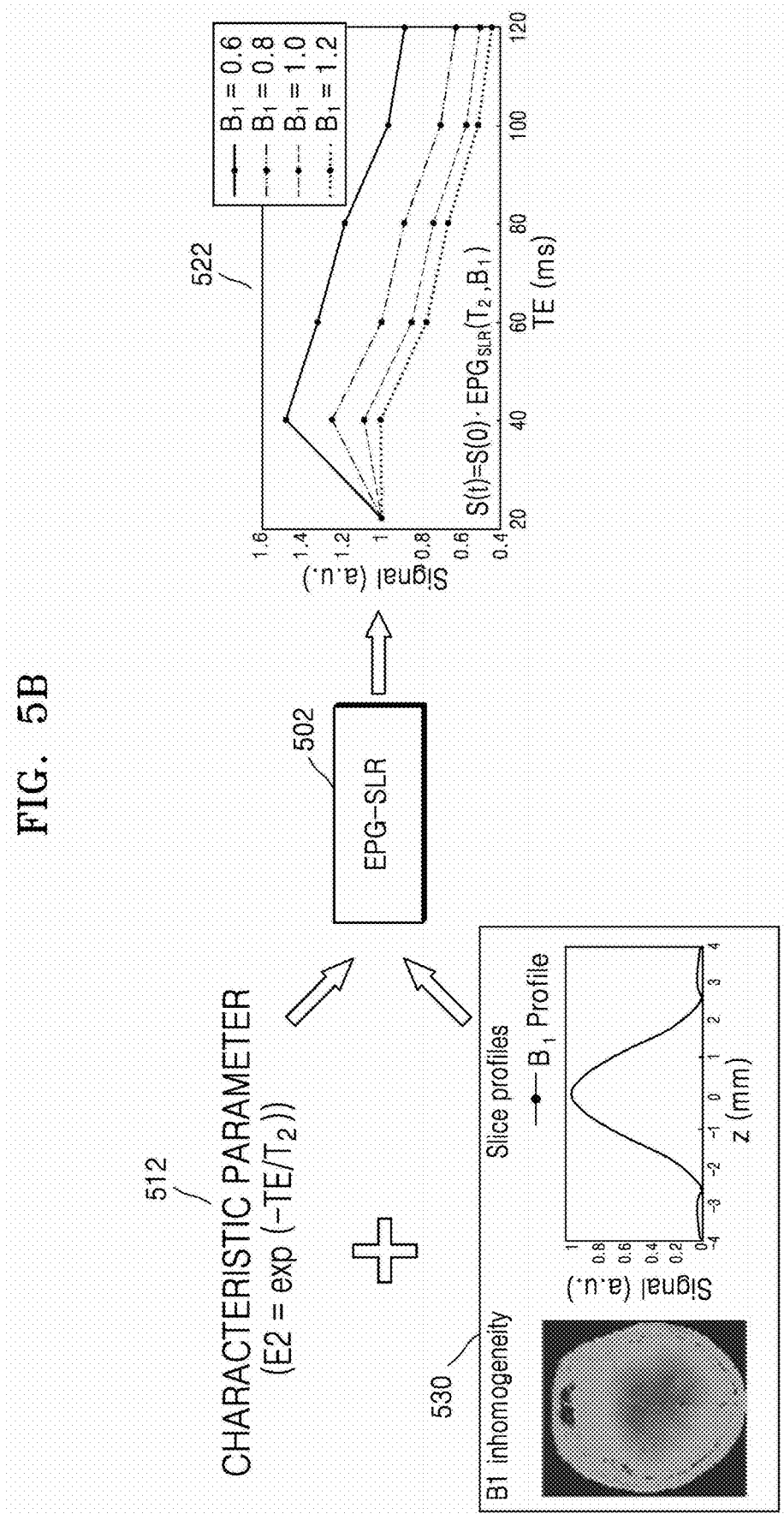
FIG. 5B illustrates an example in which an MRI apparatus generates an MR signal response based on a characteristic parameter by using an MR signal modeling equation, according to an embodiment of the disclosure.

FIG. 5B illustrates an example in which an MRI apparatus generates an MR signal response 522 based on a characteristic parameter 512 by using an MR signal modeling equation, according to an embodiment of the disclosure. In the embodiment of the disclosure shown in FIG. 5B, the MRI apparatus may overcome the problems such as an error and low accuracy of the MR signal response 520 generated via the exponential decay model shown in FIG. 5A by exploiting an EPG-SLR modeling equation 502 using RF slice profile information.

Referring to FIG. 5B, the MRI apparatus may generate synthetic data 522 that is a virtual MR signal response via simulation performed by inputting to the EPG-SLR modeling equation 502 a pair of an E2 value (an exponential value at T2 time) 512 that is a characteristic parameter at T2 time and a B1 value 530 for an RF slice profile. The synthetic data 522 may be an MR signal response in a MSE sequence. For example, the MRI apparatus may generate the synthetic data 522 via simulation represented by Equation (2) below:

$$S_{mSE}(t) = \sum_{n=1}^{N} S_{mSE}(0) \cdot EPG_{CPMG}(t; T_2, B_1, T_1, \theta_{exc}(n), \theta_{ref}(n), TE) \quad (2)$$

In Equation (2), $EPG_{CPMG}$ may be an example of a modeling equation based on an EPG simulation, B1 may be a parameter value corresponding to RF pulse inhomogeneity, and TE may be an echo spacing. $\theta_{exc}(n)$ and $\theta_{ref}(n)$ may respectively denote slice profiles of an excitation pulse and a refocusing pulse. N may be the number of points along a slice (z) direction.

According to an embodiment of the disclosure, the MRI apparatus may respectively scale the E2 value 512 and the B1 value 530 to values in preset ranges. For example, the MRI apparatus may respectively scale the E2 and B1 values 512 and 530 to ranges ([0, 1]) and ([0.5, 1.5]) and perform uniform sampling for the ranges to generate a pair of the E2 and B1 values 512 and 530. The MRI apparatus may generate a T2 mapping curve by simulating a pair of characteristic parameter values consisting of the E2 and B1 values 512 and 530 via the EPG-SLR modeling equation 502 and generate the synthetic data 522 including a plurality of curves respectively corresponding to a plurality of pairs of characteristic parameter values.

Figure 6A:
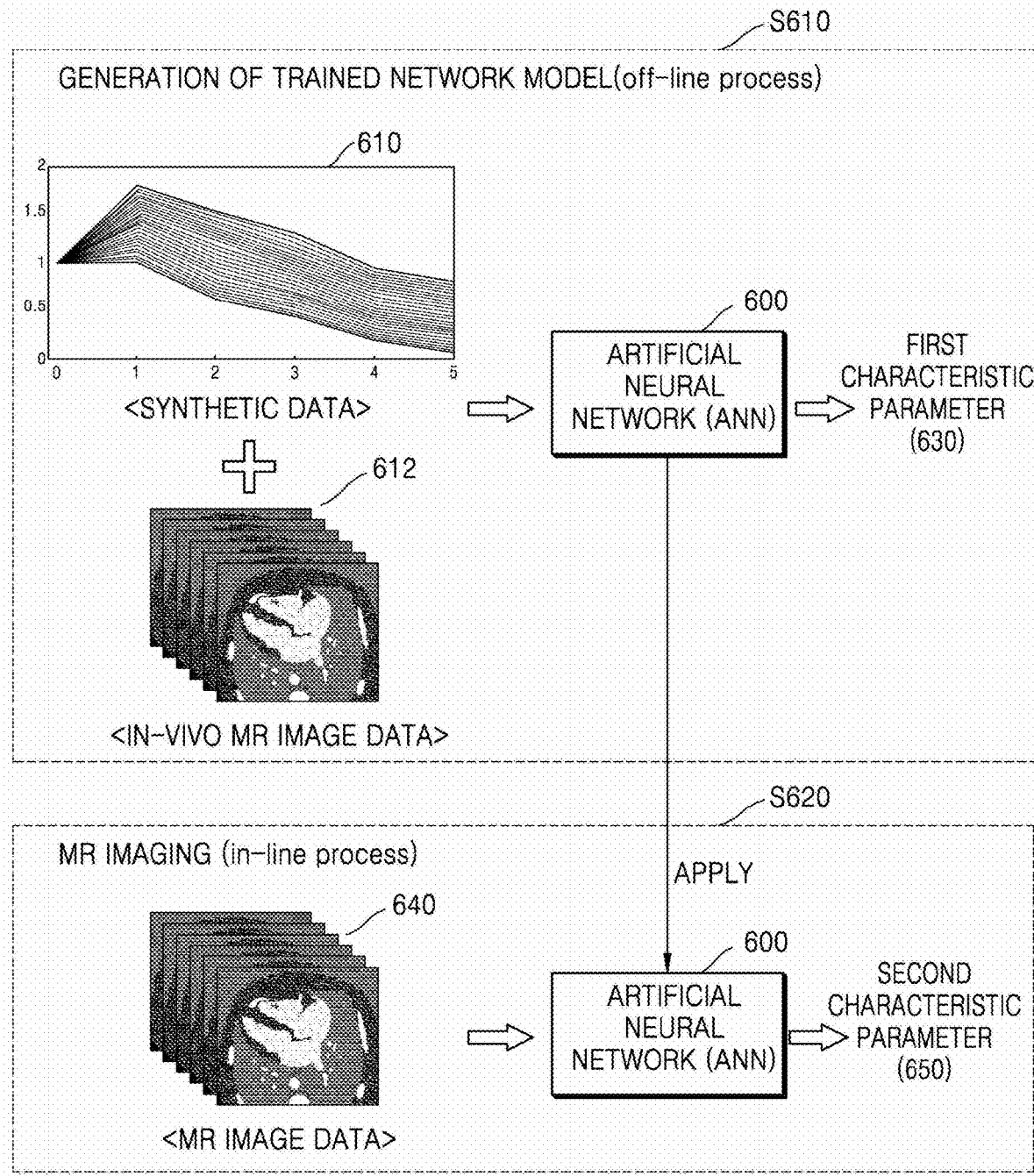
FIG. 6A illustrates an example in which an MRI apparatus acquires a characteristic parameter value from MR image data with respect to an object through training using an artificial neural network (ANN), according to an embodiment of the disclosure.

FIG. 6A illustrates an example in which an MRI apparatus acquires a characteristic parameter from MR image data with respect to an object through training using an ANN 600, according to an embodiment of the disclosure.

Referring to FIG. 6A, the MRI apparatus may perform training in two operations: an operation of generating a trained network model (S610), which is an off-line process, and an operation of perform MR imaging on the object (S620), which is an in-line process. Although FIG. 6A shows a training method using the ANN 600, embodiments of the disclosure are not limited thereto. According to an embodiment of the disclosure, the MRI apparatus may perform training by using algorithms such as SVM, linear regression, logistic regression, Naïve Bayes, decision tree, kNN algorithm, etc. Operation S610 may be a training process for generating the trained network model prior to the MR imaging of the actual object, and operation S620 may be performed together with the MR imaging of the actual object.

In this case, the training may be performed by the processor (122 of FIG. 1) of the MRI apparatus 100, but alternatively may be performed by a separate AI learning module. According to an embodiment of the disclosure, the processor 122 and the AI learning module may be integrated into a single chip.

The operation of generating the trained network model (S610) may be a training process using pre-acquired MR image data and may be performed prior to the operation of performing MR imaging of the actual object (S620). The MRI apparatus may perform training by applying to the ANN 600 at least one of synthetic data 610 generated via simulation using an MR signal modeling equation or pre-acquired MR image data 612 with respect to the object as input and a first characteristic parameter 630 as groundtruth.

The synthetic data 610 applied to the ANN 600 as input may be a set of a plurality of curves of MR signal responses generated by simulating a plurality of characteristic parameters in a preset range via an MR signal modeling equation. Descriptions of the synthetic data 610 are already provided above with respect to FIGS. 5A and 5B and thus will not be repeated below.

The MR image data 612 applied to the ANN 600 as input may be in-vivo image data pre-acquired with respect to the object. According to an embodiment of the disclosure, a multi-echo signal for each voxel in the MR image data 612 may be input to the ANN 600.

The first characteristic parameter 630 applied to the ANN 600 as groundtruth may be a parameter value corresponding to the input applied to the ANN 600, i.e., a curve in the synthetic data 610 and sample values (e.g., MR signal intensity at a plurality of TEs) for each voxel in the MR image data 612. For example, in T2 mapping, the first characteristic parameter 630 may be T2 time.

According to an embodiment of the disclosure, the MRI apparatus may form an input/output pair of an input consisting of at least one of the synthetic data 610 or the MR image data 612 and the first characteristic parameter 630 that is a groundtruth corresponding to the input and perform training by applying the formed input/output pair to the ANN 600 on a voxel-by-voxel basis.

Operation S620 is an operation of performing MR imaging on the actual object, and the process of applying MR image data acquired via the MR imaging to the trained network model acquired via the training in operation S610 may be performed together with operation S620 as an in-line process. According to an embodiment of the disclosure, the MRI apparatus may calculate a second characteristic parameter 650 by applying MR image data 640 acquired by performing the MR imaging on the object to the ANN 600 as input.

In the operation of performing the MR imaging (S620), the MRI apparatus may input the MR image data 640 with respect to the object to the ANN 600 to calculate a value of the second characteristic parameter 650 from the MR image data 640. The MRI apparatus may generate a parametric map by mapping the calculated value of the second characteristic parameter 650 on a voxel-by-voxel basis. The MRI apparatus may display the generated parametric map on the display (130 of FIG. 1).

Figure 6B:
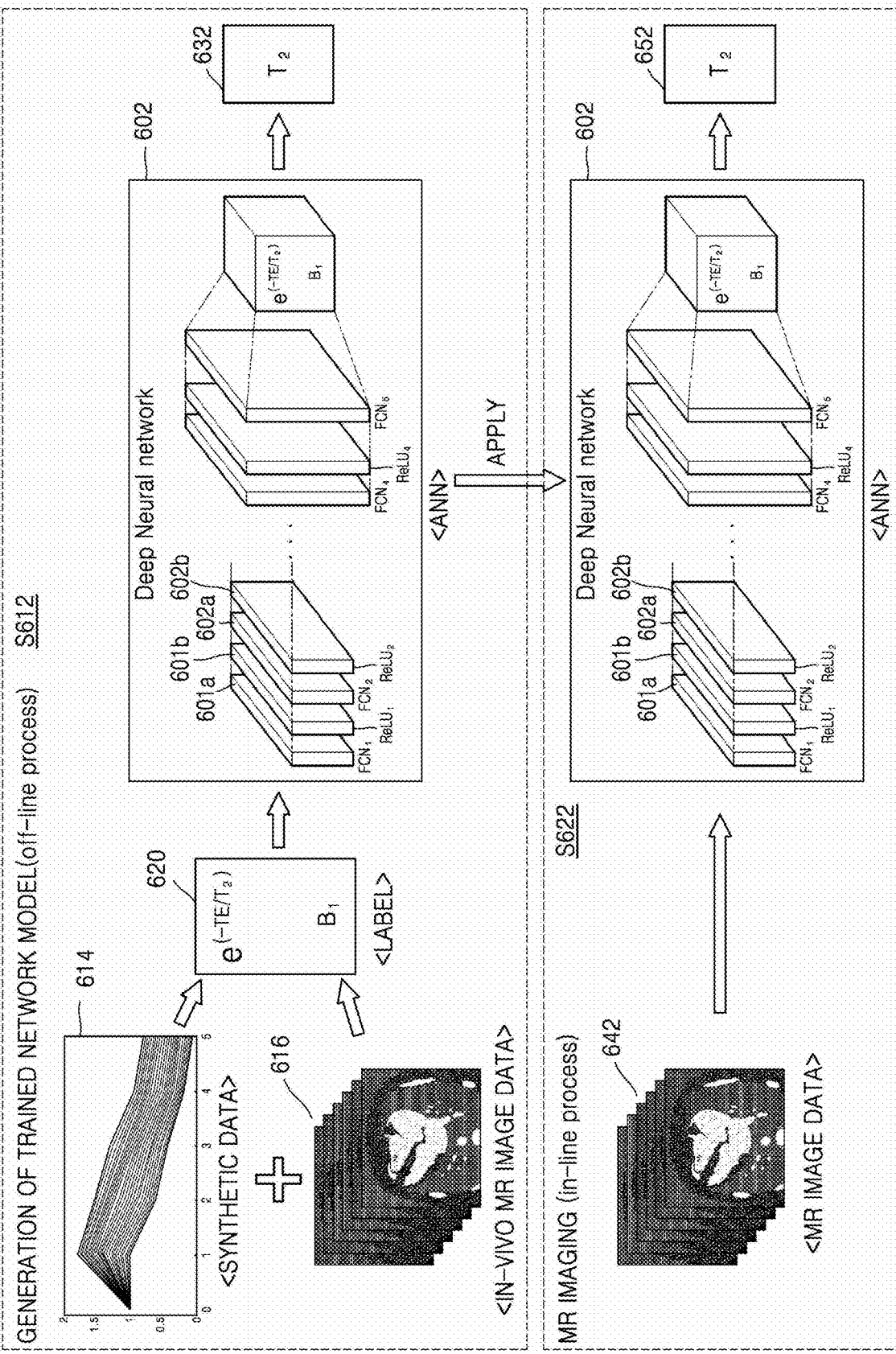
FIG. 6B illustrates an example in which an MRI apparatus acquires a characteristic parameter from MR image data with respect to an object through training using a deep neural network (DNN), according to an embodiment of the disclosure.

FIG. 6B illustrates an example in which an MRI apparatus acquires a characteristic parameter from MR image data with respect to an object through training using a deep neural network (DNN) 602, according to an embodiment of the disclosure.

Referring to FIG. 6B, the MRI apparatus may perform two processes: an off-line process that is an operation of generating a trained network model (S612) and an in-line process that is an operation of performing MR imaging on the object (S622). In operation S612, the MRI apparatus may generate the trained network model by performing training before the MR imaging of the object, and in operation S622, may generate a parametric map by using the trained network model together with the MR imaging of the actual object.

The training shown in FIG. 6B uses the DNN 602 for T2 mapping. In the operation of generating the trained network model (S612), the MRI apparatus may extract a label value 620 to be input to the DNN 602 by combining synthetic data 614 generated via simulation using an EPG-SLR model with pre-acquired in-vivo MR image data 616. According to an embodiment of the disclosure, the MRI apparatus may also extract the label value 620 by using at least one of the synthetic data 614 or the in-vivo MR image data 616.

The label value 620 may include an E2 value (an exponential value at T2 time) and a B1 value. According to an embodiment of the disclosure, the MRI apparatus may measure an intensity of a multi-echo signal for each voxel in the in-vivo MR image data 616 and estimate, on a voxel-by-voxel basis, an E2 value and a B1 value from the measured intensity of the multi-echo signal by using a nonlinear least-squares curve fitting method. The MRI apparatus may generate the label value 620 by combining curve fitting of the synthetic data 614 corresponding to the estimated E2 and B1 values.

According to an embodiment of the disclosure, the label value 620 may be scaled to a value in a preset range and may be uniformly distributed within the preset range. For example, the E2 value may be uniformly distributed within a range of [0.5, 1.5].

In the embodiment of the disclosure shown in FIG. 6B, the MRI apparatus may perform training by using a DNN model that is composed of a plurality of fully-connected network layers 601a through 605a and uses rectified linear units (ReLus) as an activation function. According to an embodiment of the disclosure, the five fully-connected network layers 601a through 605a may respectively have dimensions of 6×8, 8×16, 16×64, 64×256, and 256×2. However, the model of the DNN 602 shown in FIG. 6B is merely an example for convenience, and the type, number, and dimension of a layer in the model of the DNN 602 are not limited to those shown in FIG. 6B.

The MRI apparatus may perform training by respectively applying the label value 620 and a first T2 value 632 to the DNN 602 as input and groundtruth. The first T2 value 632 may be a parameter value related to a T2 time pre-calculated via simulation using an EPG-SLR model. According to an embodiment of the disclosure, the MRI apparatus may form a pair of the label value 620 consisting of the E2 and B1 values and the first T2 value that is the ground truth corresponding to the label value 620 and perform training by applying the formed pair to the DNN 602 voxel-by-voxel. The MRI apparatus may generate a trained network model via the training.

Operation S622 is an operation of performing MR imaging on the actual object. According to an embodiment of the disclosure, the MRI apparatus may calculate a second T2 value 652 by applying MR image data 642 acquired by performing the MR imaging on the object to the DNN 602 as input.

In the operation of performing the MR imaging (S622), the MRI apparatus may input the MR image data 642 with respect to the object to the DNN 600 to calculate the second T2 value 652 corresponding to the MR image data 640. The MRI apparatus may generate a T2 map by mapping the second T2 value 652 voxel-by-voxel. The MRI apparatus may also display the generated T2 map on the display (130 of FIG. 1).

The methods of calculating a second characteristic parameter via training using the ANN 600 of FIG. 6A and the DNN 602 of FIG. 6B and generating a parametric map by mapping a value of the second characteristic parameter may significantly reduce the processing speed compared to a method of generating a parametric map according to the related art. In particular, according to the embodiment of the disclosure described with reference to FIG. 6B, by performing training using the synthetic data 614 generated via simulation using an EPG-SLR model that is a modeling equation using an RF slice profile, it is possible to prevent degradation in accuracy of T2 mapping due to inhomogeneity of an RF pulse.

However, in the embodiments of the disclosure described with reference to FIGS. 6A and 6B, an error may be detected because the training uses regression modeling. A method of detecting an error and correcting the detected error will now be described in more detail with reference to FIGS. 7 and 8.

FIG. 7 illustrates an example in which an MRI apparatus corrects an error by using a dictionary of a characteristic parameter, according to an embodiment of the disclosure.

Referring to FIG. 7, the MRI apparatus may create a dictionary 710 of E2 and B1 values that are an output parameter value 700. The dictionary 710 may be defined as a pair of E2 and B1 values that are uniformly distributed within a preset range. According to an embodiment of the disclosure, the E2 value in the dictionary 710 may have n values along an x axis within a range of ([0,1]) while the B1 value may have m values along a y-axis within a range of ([0.5, 1.5]).

While it has been described with reference to FIG. 7 that the MRI apparatus creates the dictionary 710, embodiments of the disclosure are not limited thereto. According to an embodiment of the disclosure, the dictionary may be stored in a memory of the MRI apparatus or an external server.

The MRI apparatus may calculate a residual error value at each voxel by performing training. According to an embodiment of the disclosure, the MRI apparatus may calculate a residual error value by using a mean-square-error as a cost function and generate a residual error map 720 by mapping the calculated residual error value for each voxel.

The MRI apparatus may detect an error for each voxel by extracting a voxel at which the calculated residual error value exceeds a preset threshold. For example, the MRI apparatus may detect an error for each voxel by extracting a voxel at which a root mean square (RMS) error is greater than or equal to 0.02. In the embodiment of the disclosure shown in FIG. 7, the MRI apparatus may detect a first voxel 722 at which an RMS error exceeds a preset threshold in the residual error map 720.

The MRI apparatus may perform dictionary-matching by replacing a value of a voxel at which an error is detected with a characteristic parameter value of a corresponding voxel in the dictionary 710. The MRI apparatus may correct an error for each voxel by performing the dictionary-matching. According to an embodiment of the disclosure, the MRI apparatus may replace a value of the first voxel 722 with a first dictionary value 712 corresponding to a position of the first voxel 722 in the dictionary 710.

FIG. 8 is a flowchart of a method, performed by an MRI apparatus, of correcting an error by using a dictionary of a characteristic parameter, according to an embodiment of the disclosure.

The MRI apparatus performs training to calculate a characteristic parameter value for each voxel in MR image data with respect to an object (S810). In T2 mapping via an EPG-SLR modeling equation, the characteristic parameter value may include an E2 value (an exponential value at T2 time) and a B1 value.

The MRI apparatus creates a dictionary of a characteristic parameter value in a preset range (S820). According to an embodiment of the disclosure, the MRI apparatus may generate a dictionary consisting of a pair of E2 and B1 values uniformly distributed within a preset range.

According to an embodiment of the disclosure, the dictionary may be stored in a memory of the MRI apparatus or an external server. In this case, operation S820 may not be performed.

The MRI apparatus detects a voxel at which a residual error value with respect to a calculated output value exceeds a preset threshold (S830).

The MRI apparatus corrects an error by replacing a value of the voxel at which an error is detected with a characteristic parameter value of a corresponding voxel in the dictionary (S840). The MRI apparatus may acquire a characteristic parameter value corresponding to a voxel at which an error is detected from the dictionary and then replace the value of the voxel at which the error is detected with the acquired characteristic parameter value.

Figure 9:
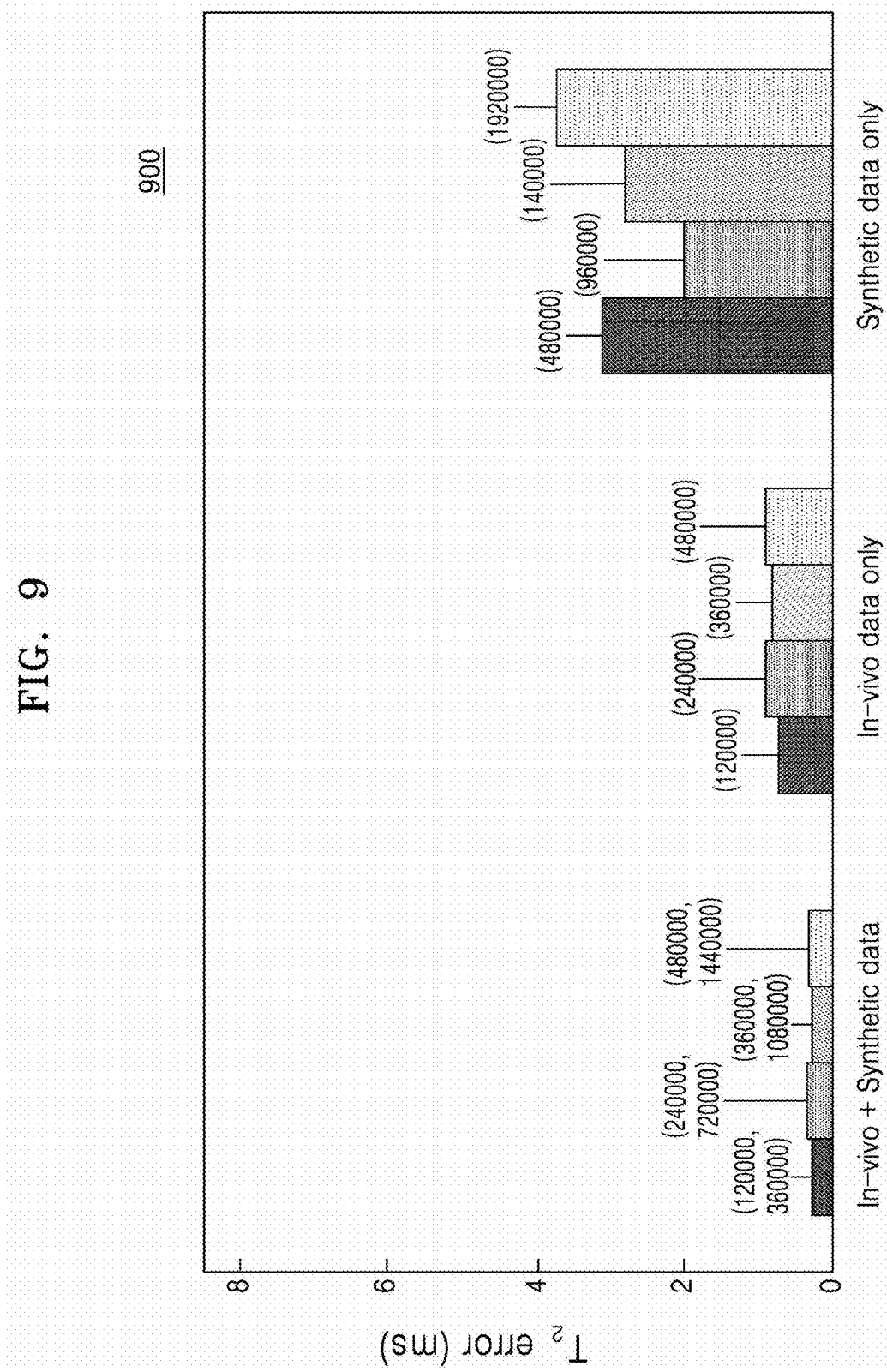
FIG. 9 illustrates a graph of an average error in results obtained when an MRI apparatus performs training by using different pieces of input data, according to an embodiment of the disclosure.

FIG. 9 illustrates a graph 900 of an average T2 error in results obtained when an MRI apparatus performs training by using different pieces of input data, according to an embodiment of the disclosure.

Referring to the graph 900 shown in FIG. 9, a T2 error value in training using a combination of synthetic data and in-vivo MR image data with respect to an object is less than a T2 error value in training using only the in-vivo MR image data or only the synthetic data. In the graph 900, each number in parentheses may indicate the amount of data used for training. As seen in the graph 900, the amount of data used for training does not significantly affect a T2 error value.

As seen in the graph 900, a T2 error value in the result of training using only the in-vivo MR image data with respect to the object is greater than a T2 error value in the result of training using only the synthetic data but is similar to a T2 error value in the result of training using a combination of the in-vivo MR image data and the synthetic data. The difference in a T2 error value may be attributed to the synthetic data being generated based on a decay of T2 only. Furthermore, noise characteristics may vary according to parallel imaging techniques or reconstruction methods using a multi-coil system. In the case of training using in-vivo MR image data, noise characteristics may be trained because the in-vivo MR image data contains noise. On the other hand, in the case of training with synthetic data, errors may occur frequently and prediction accuracy may be degraded due to limited ranges of E2 and B1 values and lack of data.

Figure 10:
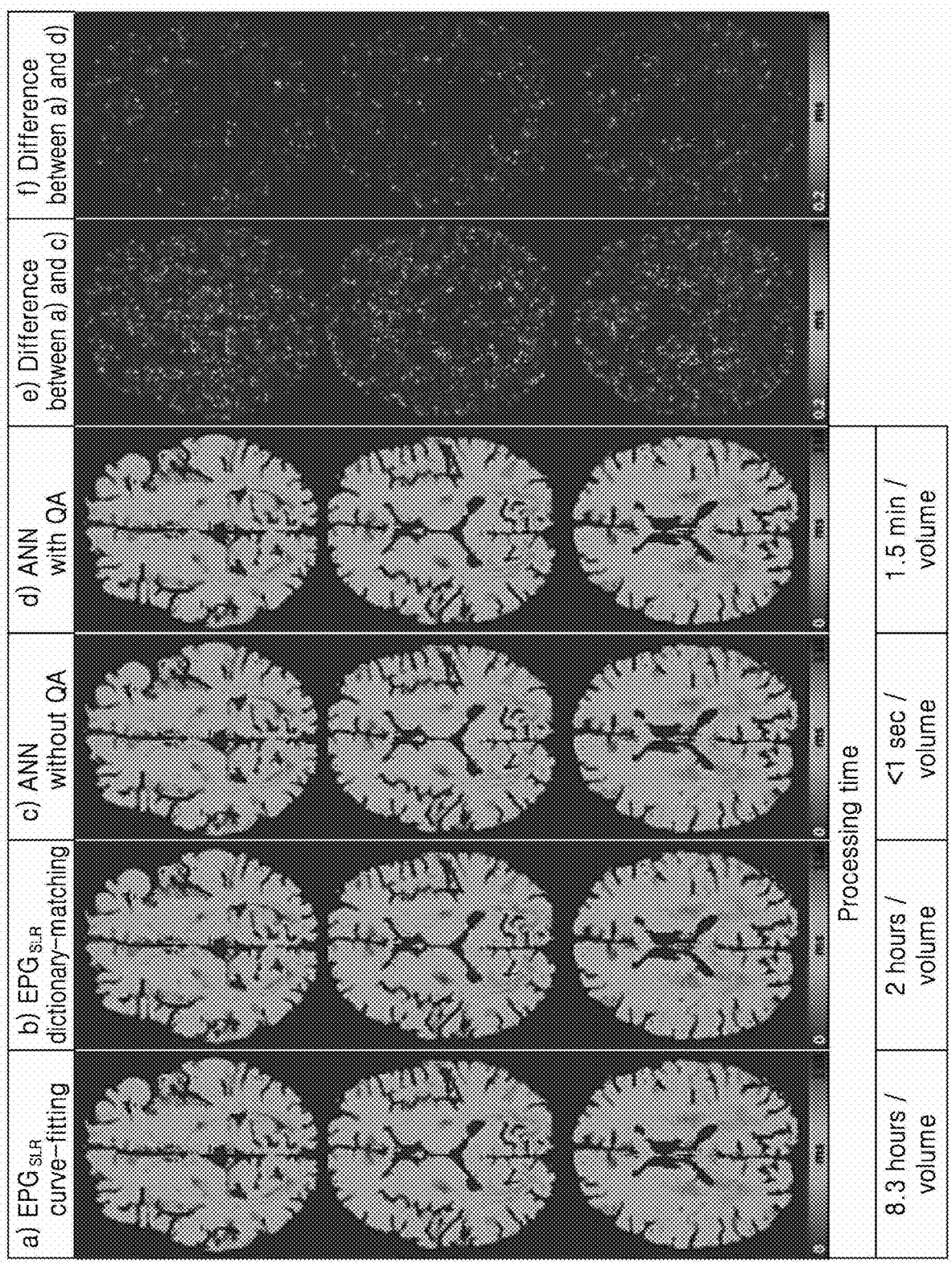
FIG. 10 illustrates T2 maps respectively generated by an MRI apparatus when using an MR signal modeling equation and when using an ANN and the amount of time required to generate the corresponding T2 maps, according to an embodiment of the disclosure.

FIG. 10 illustrates T2 maps respectively generated by an MRI apparatus when using an MR signal modeling equation and when using an ANN and the amount of time required to generate the corresponding T2 maps, according to an embodiment of the disclosure.

As seen on FIG. 10, training c) via an ANN without error correction ('ANN without Quality Assurance (QA)') requires the shortest time less than 1 second to process the training result. Training d) via an ANN with dictionary-based error correction ('ANN with QA') requires the next shortest time about 1.5 minutes to process the training result. Training a) with curve fitting using an EPG-SLR modeling equation requires a very long processing time of 8.3 hours for modeling.

In e) of FIG. 10, a difference between a) and c) means an error between the results of training via simulation using EPG-SLR modelling and training without error correction. In f) of FIG. 10, a difference between a) and d) means an error between the results of the training via simulation using EPG-SLR modeling and the training with error correction. The error shown in e) (the difference between a) and c)) is greater than the error shown in f) (the difference between a) and d)), which means that training d) with error correction provides a higher level of accuracy than training a) and training c).

Referring to FIGS. 9 and 10, an MRI apparatus and method of performing parametric mapping via training using an ANN and error correction according to embodiments of the disclosure may significantly reduce the processing time and improve accuracy compared to a parametric mapping method of the related art.

The embodiments of the disclosure may be implemented as a software program including instructions stored in computer-readable storage media.

A computer may refer to a device capable of retrieving instructions stored in the computer-readable storage media and performing operations according to embodiments of the disclosure in response to the retrieved instructions, and may include MRI apparatuses according to the embodiments of the disclosure.

The computer-readable storage media may be provided in the form of non-transitory storage media. In this case, the term 'non-transitory' only means that the storage media do not include signals and are tangible, and the term does not distinguish between data that is semi-permanently stored and data that is temporarily stored in the storage media.

In addition, MRI apparatuses and methods of operating the same according to embodiments of the disclosure may be included in a computer program product when provided. The computer program product may be traded, as a commodity, between a seller and a buyer.

The computer program product may include a software program and a computer-readable storage medium having stored thereon the software program. For example, the computer program product may include a product (e.g. a downloadable application) in the form of a software program electronically distributed by a manufacturer of an MRI apparatus or through an electronic market (e.g., Google Play Store™, and App Store™). For such electronic distribution, at least a part of the software program may be stored on the storage medium or may be temporarily generated. In this case, the storage medium may be a storage medium of a server of the manufacturer, a server of the electronic market, or a relay server for temporarily storing the software program.

In a system consisting of a server and a device (e.g., an MRI apparatus), the computer program product may include a storage medium of the server or a storage medium of the device. Alternatively, in a case where a third device (e.g., a smartphone) is connected to the server or device through a communication network, the computer program product may include a storage medium of the third device. Alternatively, the computer program product may include a software program that is transmitted from the server to the device or the third device or that is transmitted from the third device to the device.

In this case, one of the server, the device, and the third device may execute the computer program product to perform methods according to embodiments of the disclosure. Alternatively, two or more of the server, the device, and the third device may execute the computer program product to perform the methods according to the embodiments of the disclosure in a distributed manner.

For example, the server (e.g., a cloud server, an AI server, or the like) may run the computer program product stored therein to control the device communicating with the server to perform the methods according to embodiments of the disclosure.

As another example, the third device may execute the computer program product to control the device communicating with the third device to perform the methods according to the embodiments of the disclosure.

In a case where the third device executes the computer program product, the third device may download the computer program product from the server and execute the downloaded computer program product. Alternatively, the third device may execute the computer program product that is pre-loaded therein to perform the methods according to the embodiments of the disclosure.

Embodiments of the disclosure may be implemented through non-transitory computer-readable recording media having recorded thereon computer-executable instructions and data. The instructions may be stored in the form of program codes, and when executed by a processor, generate a predetermined program module to perform a specific operation. Furthermore, when being executed by the processor, the instructions may perform specific operations according to the embodiments.

While one or more embodiments of the disclosure have been described with reference to the figures, it will be understood by those of ordinary skill in the art that various changes in form and details may be made therein without departing from the spirit and scope of the disclosure as defined by the following claims. Accordingly, the above embodiments and all aspects thereof are examples only and are not limiting.

What is claimed is:

1. A method of generating a parametric map based on magnetic resonance (MR) signal data, the method comprising:
    acquiring a trained network model by performing training in which MR signal data generated using a magnetic resonance imaging (MRI) method and an MR signal model is applied to an artificial neural network as input and a first characteristic parameter value calculated via the MR signal model is applied to the artificial neural network as groundtruth;
    acquiring MR image data by scanning an object; applying the MR image data to the trained network model; and calculating, using the trained network model and based on the MR image data, a second characteristic parameter value with respect to the MR image data, wherein the MR signal data comprises synthetic data generated via simulation using a parameter value representing an extent of decay of in-vivo MR image data at a specific echo time (TE) and a radio frequency slice profile and the in-vivo MR image data pre-acquired with respect to the object.

2. The method of claim 1, wherein the MR signal data is an MR signal response simulated using an MR signal modeling equation, and wherein the MR signal modeling equation is based on an MR sequence for capturing an MR image of the object.

3. The method of claim 2, wherein the MR signal modeling equation is an equation for simulating the MR signal data by using the first characteristic parameter value and the radio frequency slice profile used for capturing the MR image of the object.

4. The method of claim 1, wherein the performing of the training comprises performing the training by applying to the artificial neural network at least one of the synthetic data or the pre-acquired in-vivo MR image data as input and the first characteristic parameter value as groundtruth.

5. The method of claim 4, wherein the performing training comprises:
    associating as a pair: i) the synthetic data and the pre-acquired in-vivo MR image data, and ii) the groundtruth; and
    applying the pair to the artificial neural network on a voxel-by-voxel basis with respect to the in-vivo MR image data.

6. The method of claim 1, further comprising generating a parametric map based on the calculated second characteristic parameter value,
    wherein the parametric map comprises at least one of a T1 map, a T2 map, a T1rho map, or a proton density (PD) map.

7. The method of claim 1, further comprising:
    calculating, based on the training, a residual error value for a voxel of a plurality of voxels; and
    detecting an error by extracting the voxel based on the residual error value exceeding a preset threshold.

8. The method of claim 7, further comprising:
    creating a dictionary of the first characteristic parameter value in a preset range by using the MR signal model;
    acquiring from the dictionary the first characteristic parameter value corresponding to the voxel at which the error is detected; and
    correcting the error by replacing a value of the voxel at which the error is detected with the acquired first characteristic parameter value.

9. A magnetic resonance imaging (MRI) apparatus for generating a parametric map based on magnetic resonance (MR) signal data, the apparatus comprising:
    a radio frequency coil configured to acquire, from at least one radio frequency channel coil, an MR signal emitted from an object;
    a memory storing instructions for processing the MR signal received from the radio frequency coil; and
    a processor configured to execute the stored instructions to:
    generate a trained network model by performing training in which MR signal data generated using an MRI method and an MR signal model is applied to an artificial neural network as input and a first characteristic parameter value calculated via the MR signal model is applied to the artificial neural network as groundtruth;
    acquire MR image data by scanning the object; apply the MR image data to the trained network model; and
    calculate, using the trained network model and based on the MR image data, a second characteristic parameter value with respect to the MR image data, wherein the MR signal data comprises synthetic data generated via simulation using a parameter value representing an extent of decay of in-vivo MR image data at a specific echo time (TE) and a radio frequency slice profile and the in-vivo MR image data pre-acquired with respect to the object.

10. The MRI apparatus of claim 9, wherein the MR signal data is an MR signal response simulated using an MR signal modeling equation, and wherein the MR signal modeling equation is based on an MR sequence for capturing an MR image of the object.

11. The MRI apparatus of claim 10, wherein the MR signal modeling equation is an equation for simulating the MR signal data by using the first characteristic parameter value and the radio frequency slice profile used for capturing the MR image of the object.

12. The MRI apparatus of claim 9, wherein the processor is further configured to execute the stored instructions to perform the training by applying to the artificial neural network at least one of the synthetic data or the pre-acquired in-vivo MR image data as input and the first characteristic parameter value as groundtruth.

13. The MRI apparatus of claim 12, wherein the processor is further configured to execute the stored instructions to:
associate as a pair: i) the synthetic data and the pre-acquired in-vivo MR image data, ii) the groundtruth; and
generate the trained network model by performing the training by applying the pair to the artificial neural network on a voxel-by-voxel basis with respect to the in-vivo MR image data.

14. The MRI apparatus of claim 9, wherein the processor is further configured to execute the stored instructions to generate a parametric map based on the calculated second characteristic parameter value, and
wherein the parametric map comprises at least one of a T1 map, a T2 map, a T1rho map, or a proton density (PD) map.

15. The MRI apparatus of claim 14, further comprising a display,
wherein the processor is further configured to execute the stored instructions to control the display to display the parametric map.

16. The MRI apparatus of claim 9, wherein the processor is further configured to execute the stored instructions to:
calculate, based on the training, a residual error value for a voxel of a plurality of voxels; and
detect an error for the voxel by extracting the voxel, wherein the residual error value exceeds a preset threshold.

17. The MRI apparatus of claim 16, wherein the processor is further configured to execute the stored instructions to:
create a dictionary of the first characteristic parameter value in a preset range by using the MR signal model;
acquire from the dictionary the first characteristic parameter value corresponding to the voxel at which the error is detected; and
correct the error by replacing a value of the voxel at which the error is detected with the acquired first characteristic parameter value.

18. A computer program product comprising a non-transitory computer-readable storage medium, wherein the non-transitory computer-readable storage medium comprises instructions for performing a method of operating a magnetic resonance imaging (MRI) apparatus, the method comprising:
acquiring a trained network model by performing training in which magnetic resonance (MR) signal data generated using an MRI method and an MR signal model is applied to an artificial neural network as input and a first characteristic parameter value calculated via the MR signal model is applied to the artificial neural network as groundtruth;
acquiring MR image data by scanning an object; applying the MR image data to the trained network model; and calculating, using the trained network model and based on the MR image data, a second characteristic parameter value with respect to the MR image data,
wherein the MR signal data comprises synthetic data generated via simulation using a parameter value representing an extent of decay of in-vivo MR image data at a specific echo time (TE) and a radio frequency slice profile and the in-vivo MR image data pre-acquired with respect to the object.

* * * * *